(12) United States Patent
Mendelson et al.

(10) Patent No.: US 11,903,828 B2
(45) Date of Patent: Feb. 20, 2024

(54) TRANSCATHETER PROSTHETIC HEART VALVE DELIVERY SYSTEM WITH LATERAL OFFSET CONTROL

(71) Applicant: Medtronic Vascular, Inc., Santa Rosa, CA (US)

(72) Inventors: Jill Mendelson, San Francisco, CA (US); Michele Silver, Healdsburg, CA (US); Michael Gloss, Minneapolis, MN (US); Timothy Groen, Rush City, CA (US); Paul Rothstein, Elk River, MN (US); Jeffrey Sandstrom, Scandia, MN (US); Phil Haarstad, Minneapolis, MN (US); Joel Racchini, Edina, MN (US); David Blaeser, Minneapolis, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 691 days.

(21) Appl. No.: 16/934,119

(22) Filed: Jul. 21, 2020

(65) Prior Publication Data

US 2020/0345490 A1 Nov. 5, 2020

Related U.S. Application Data

(62) Division of application No. 15/614,890, filed on Jun. 6, 2017, now Pat. No. 10,765,513.

(Continued)

(51) Int. Cl.
*A61F 2/24* (2006.01)
*A61F 2/95* (2013.01)
(Continued)

(52) U.S. Cl.
CPC .......... *A61F 2/2427* (2013.01); *A61F 2/2436* (2013.01); *A61F 2/2439* (2013.01);
(Continued)

(58) Field of Classification Search
CPC .... A61F 2/2427; A61F 2/2436; A61F 2/2439; A61F 2/243; A61F 2/2433; A61F 2/95;
(Continued)

(56) References Cited

U.S. PATENT DOCUMENTS

| 10,420,642 B2 | 9/2019 | Gloss et al. |
| 2002/0151953 A1 | 10/2002 | Chobotov |

(Continued)

FOREIGN PATENT DOCUMENTS

| CN | 101036602 | 9/2007 |
| CN | 101045023 | 10/2007 |

(Continued)

OTHER PUBLICATIONS

PCT/US2017/036082, The International Search Report and Written Opinion of the International Searching Authority, dated Aug. 10, 2017.

*Primary Examiner* — Diane D Yabut
(74) *Attorney, Agent, or Firm* — Wentsler LLC

(57) ABSTRACT

Delivery devices for a stented prosthetic heart valve. The delivery device includes a spindle, at least one cord, and a lateral control feature. The cord is tensioned to crimp the prosthesis to a compressed condition for delivery to a target site. Tension is lessened to allow the prosthesis to self-expand. In a tethered and expanded state in which the prosthesis has self-expanded and is connected to the spindle by the cord, the lateral control feature directs the spindle to a prescribed location relative to the prosthesis appropriate for a functional evaluation of the prosthesis. In some embodiments, the spindle is directed to a center of the prosthesis; in other embodiments, the spindle is held at a commissure of the prosthesis. The lateral control features of the present disclosure assume numerous forms.

13 Claims, 25 Drawing Sheets

Related U.S. Application Data

(60) Provisional application No. 62/346,039, filed on Jun. 6, 2016.

(51) Int. Cl.
*A61F 2/07* (2013.01)
*A61F 2/962* (2013.01)

(52) U.S. Cl.
CPC ............... *A61F 2/95* (2013.01); *A61F 2/07* (2013.01); *A61F 2/243* (2013.01); *A61F 2/2418* (2013.01); *A61F 2/9517* (2020.05); *A61F 2/962* (2013.01); *A61F 2230/0063* (2013.01)

(58) Field of Classification Search
CPC ........ A61F 2/9522; A61F 2/954; A61F 2/958; A61F 2/962; A61F 2/9517; A61F 2002/9505; A61F 2002/9511; A61F 2002/9534
See application file for complete search history.

(56) References Cited

U.S. PATENT DOCUMENTS

| | | | |
|---|---|---|---|
| 2005/0119722 A1* | 6/2005 | Styrc | A61F 2/95 606/108 |
| 2006/0173524 A1* | 8/2006 | Salahieh | A61F 2/2418 623/1.11 |
| 2007/0100427 A1 | 5/2007 | Perouse | |
| 2007/0112355 A1 | 5/2007 | Salahieh et al. | |
| 2007/0203575 A1* | 8/2007 | Forster | A61F 2/2439 623/2.11 |
| 2009/0099640 A1 | 4/2009 | Weng | |
| 2010/0286768 A1 | 11/2010 | Alkhatib | |
| 2011/0040366 A1 | 2/2011 | Goetz et al. | |
| 2012/0277734 A1 | 11/2012 | Goetz et al. | |
| 2013/0096664 A1 | 4/2013 | Goetz et al. | |
| 2013/0096670 A1 | 4/2013 | Goetz et al. | |
| 2013/0103131 A1 | 4/2013 | Goetz et al. | |
| 2013/0245752 A1 | 9/2013 | Goetz et al. | |
| 2013/0268048 A1 | 10/2013 | Watson | |
| 2013/0325101 A1 | 12/2013 | Goetz et al. | |
| 2013/0338755 A1 | 12/2013 | Goetz et al. | |
| 2015/0112430 A1 | 4/2015 | Creaven et al. | |

FOREIGN PATENT DOCUMENTS

| | | |
|---|---|---|
| CN | 101283937 | 10/2008 |
| DE | 102009055969 | 6/2011 |
| WO | 2009091509 | 7/2009 |
| WO | 20170106161 | 6/2017 |

\* cited by examiner

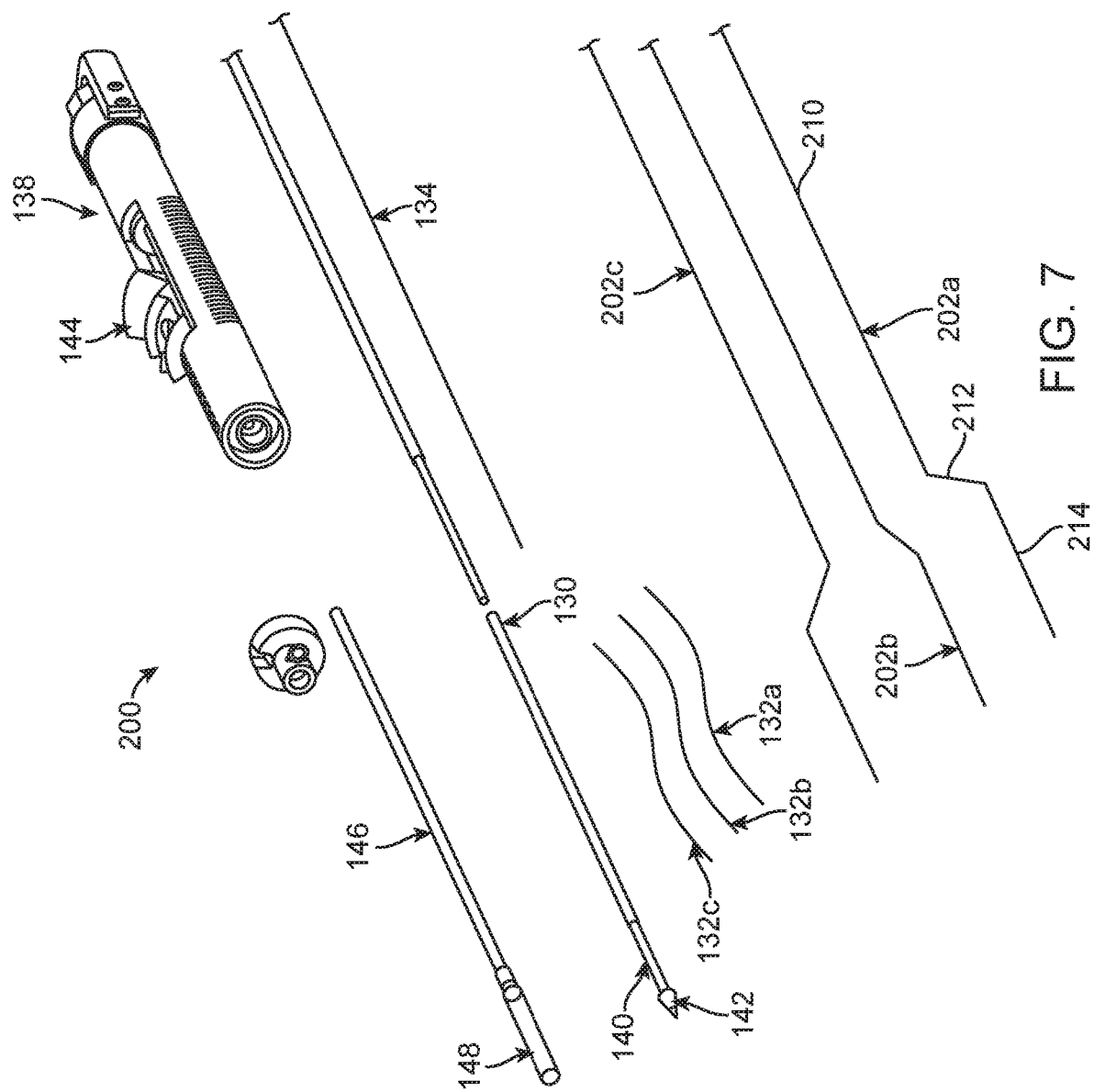

TRANSCATHETER PROSTHETIC HEART VALVE DELIVERY SYSTEM WITH LATERAL OFFSET CONTROL

CROSS-REFERENCE TO RELATED APPLICATIONS

This application is a Divisional application of Ser. No. 15/614,890, filed on Jun. 6, 2017, entitled, "TRANSCATHETER PROSTHETIC HEART VALVE DELIVERY SYSTEM WITH LATERAL OFFSET CONTROL," now allowed, which claims the benefit of the filing date of U.S. Provisional Patent Application Ser. No. 62/346,039, filed Jun. 6, 2016, entitled "TRANSCATHETER PROSTHETIC HEART VALVE DELIVERY SYSTEM WITH LATERAL OFFSET CONTROL," the entire teachings of which are incorporated herein by reference.

BACKGROUND

The present disclosure relates to transcatheter stented prosthetic heart valve delivery and deployment. More particularly, it relates to transcatheter delivery systems, devices and methods affording control over a lateral position of the prosthetic heart valve relative to the delivery device during deployment at a target site.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With one type of stented prosthetic heart valve designs, the stent frame is formed to be self-expanding. The valved stent is crimped down to a desired size and held in that compressed state within a sheath or by other means for transluminal delivery. Retracting the sheath (or other release operation) from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

SUMMARY

With some recently considered transcatheter delivery devices and methods, the prosthetic heart valve is compressed and held over a spindle of the device by one or more sutures (or similar material). To deploy the prosthesis, tension in the sutures is slowly released. While viable, these and similar techniques may not afford control over a lateral position of the prosthetic heart valve relative to the spindle as the prosthesis is being deployed.

The inventors of the present disclosure recognize that a need exists for transcatheter prosthetic heart valve delivery systems and methods that overcome one or more of the above-mentioned problems.

Some aspects of the present disclosure are directed toward delivery devices for a stented prosthetic heart valve. The delivery device includes a spindle, at least one cord, and a lateral control feature. The cord is tensioned to cinch the stented prosthetic heart valve to a compressed condition for delivery to a target site. Tension is subsequently lessened to allow the prosthesis to self-expand. In a tethered and expanded state in which the stented prosthetic heart valve has self-expanded and remains connected to the spindle by the cord, the lateral control feature directs the spindle to a prescribed location relative to the prosthesis appropriate for a functional evaluation (e.g., hemodynamics) of the prosthesis. In some embodiments, the spindle is directed to a center of the prosthesis; in other embodiments, the spindle is held at a commissure of the prosthesis. Regardless, in some embodiments, the stented prosthetic heart valve can be re-compressed from the tethered and expanded state in response to the functional evaluation. The lateral control features of the present disclosure can assume numerous forms.

BRIEF DESCRIPTION OF THE DRAWINGS

FIG. 7 is an exploded, perspective view of another delivery device in accordance with principles of the present disclosure;

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure is described with reference to preferred embodiments, workers skilled in the art will recognize that changes can be made in form and detail without departing from the spirit and scope of the present disclosure.

As described below, some aspects of the present disclosure relate to transcatheter valve delivery devices utilizing one or more flexible cords (e.g., sutures, wires, filaments, etc.) to compress and retain a stented prosthetic heart valve during delivery to a target site. By way of background, stented prosthetic heart valves useful with the delivery devices of the present disclosure can be a bioprosthetic heart valve having tissue leaflets or a synthetic heart valve having polymeric, metallic or tissue-engineered leaflets, and can be specifically configured for replacing any of the four valves of the human heart, or to replace a failed bioprosthesis, such as in the area of an aortic valve or mitral valve, for example.

In general terms, the stented prosthetic heart valves useful with the devices and methods of the present disclosure include a stent or stent frame maintaining a valve structure (tissue or synthetic), with the stent frame having a normal, expanded condition or arrangement and collapsible to a compressed condition or arrangement when loaded to a delivery device. The stent frame is normally constructed to self-deploy or self-expand when released from the delivery device. The stents or stent frames are support structures that comprise a number of struts or wire segments arranged relative to each other to provide a desired compressibility and strength to the prosthetic heart valve. The struts or wire segments are arranged such that they are capable of transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1A:
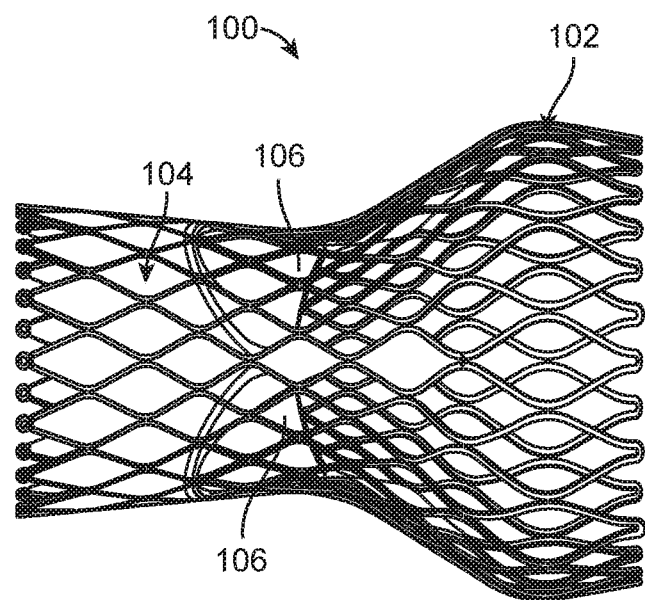
FIG. 1A is a side view of a stented prosthetic heart valve useful with the delivery devices of the present disclosure and in a normal, expanded condition.
Figure 1B:
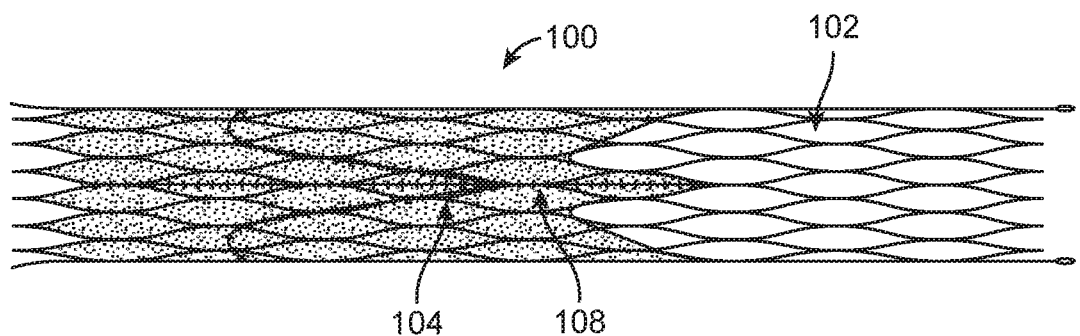
FIG. 1B is a side view of the stented prosthetic heart valve of FIG. 1A in a compressed condition.

With the above understanding in mind, one simplified, non-limiting example of a stented prosthetic heart valve 100 useful with tools and methods of the present disclosure is illustrated in FIG. 1A. As a point of reference, the stented prosthetic heart valve 100 is shown in a normal or expanded condition in the view of FIG. 1A; FIG. 1B illustrates the stented prosthetic heart valve 100 in a compressed condition (e.g., when crimped or collapsed to a delivery device as described below). The stented prosthetic heart valve 100 includes a stent or stent frame 102 and a valve structure 104. The stent frame 102 can assume any of the forms mentioned above, and is generally constructed to be self-expandable from the compressed condition (FIG. 1B) to the normal, expanded condition (FIG. 1A).

The valve structure 104 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 104 can be formed, for example, from bovine, porcine, equine, ovine and/or other suitable animal tissues. In some embodiments, the valve structure 104 can be formed, for example, from heart valve tissue, pericardium, and/or other suitable tissue. In some embodiments, the valve structure 104 can include or form one or more leaflets 106. For example, the valve structure 104 can be in the form of a tri-leaflet bovine pericardium valve, a bi-leaflet valve, or another suitable valve. In some constructions, the valve structure 104 can comprise two or three leaflets that are fastened together at enlarged lateral end regions to form commissural joints, with the unattached edges forming coaptation edges of the valve structure 104. The leaflets 106 can be fastened to a skirt that in turn is attached to the frame 102. The side-by-side arrangement of the leaflets 106 establishes commissures 108, one of which is identified in FIG. 1B.

With the one exemplary construction of FIGS. 1A and 1B, the stented prosthetic heart valve 100 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). Thus, in the various delivery device embodiments described below, where reference is made to the stented prosthetic heart valve (or prosthesis) 100, a shape of the prosthesis 100 is generically illustrated, reflecting that the prosthesis 100 can assume any shape in the normal, expanded condition.

Figure 2:
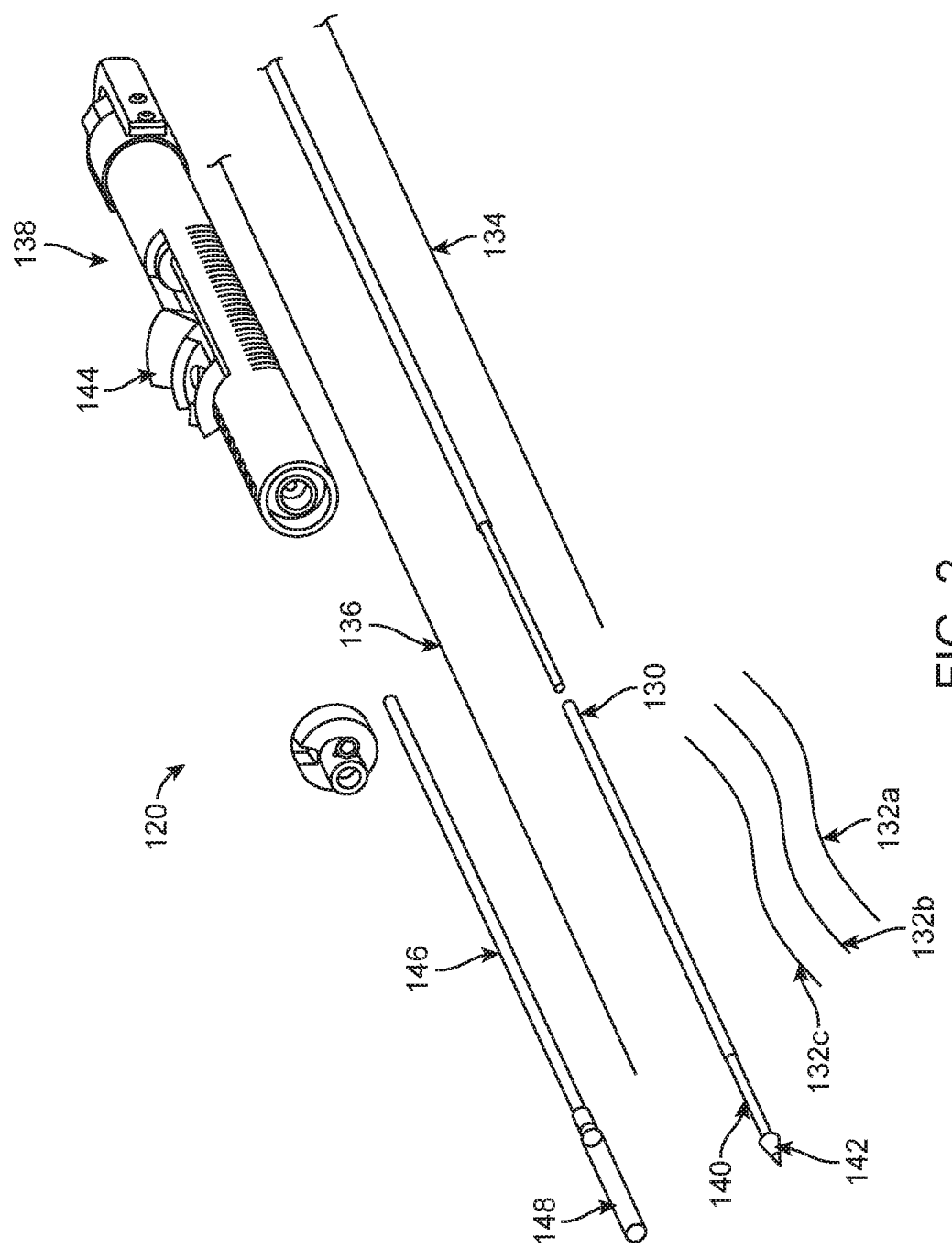
FIG. 2 is a perspective, exploded view of components of a delivery device in accordance with principles of the present disclosure.

By way of further background, FIG. 2 illustrates one non-limiting example of general components of a delivery device 120 with which some embodiments of the present disclosure are useful. The delivery device 120 includes an inner shaft 130, a plurality of cords (such as cords 132a-132c), an optional tension control rod 134, an optional release pin 136, and a handle assembly 138. The inner shaft 130 extends from the handle assembly 138 and includes or carries a spindle 140 terminating at or connected to a tip 142. Lumens (not shown) are defined in the inner shaft 130 (and extend to the spindle 140). The tension control rod 134 is connected to the handle assembly 138 and is slidably disposed within one of the lumens of the inner shaft 130. As described in greater detail below, the cords 132a-132c (e.g., sutures, wires, filaments, etc.) are each coupled at a fixed end thereof to the tension control rod 134, and extend through a respective opening in the inner shaft 130. Where provided, the release pin 136 is also connected to the handle assembly 138, and is slidably disposed within another lumen of the inner shaft 130 for selectively engaging and releasing a free end of the each of the cords 132a-132c. The handle assembly 138 includes one or more actuators 144 for user-prompted longitudinal movement of the tension control rod 134 and of the release pin 136 relative to each other and relative to the inner shaft 130. The handle assembly 138 can incorporate additional control mechanisms actuating other optional components of the delivery device 120. For example, an outer sheath assembly 146 is optionally provided, forming a capsule 148 that can be slidably disposed over the inner shaft 130.

Figure 3:
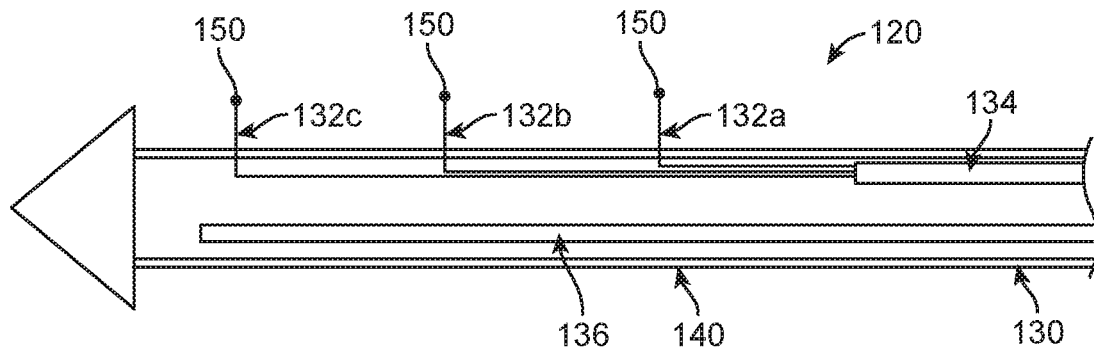
FIG. 3 is a simplified cross-sectional view of a portion of the delivery device of FIG. 2 upon final assembly.

Assembly of the delivery device 120 is generally reflected by the simplified cross-sectional representation of FIG. 3. As a point of reference, for ease of illustration, individual lumens formed within the inner shaft spindle 140 are not shown in FIG. 3 or in any other simplified cross-sectional representation of the present disclosure. The tension control rod 134 is connected to a fixed end of the each of the cords 132a-132c. The cords 132a-132c are flexible and substantially inextensible bodies (e.g., sutures, wires, filaments, etc.). The cords 132a-132c extend from the tension control rod 134, and individually pass through a respective hole or port (not shown) in the spindle 140. As identified in FIG. 3, each of the cords 132a-132c terminates at a free end 150. With embodiments in which three of the cords 132a-132c are provided, relative to the arrangement of FIG. 3, the first cord 132a serves as a proximal cord, the second cord 132b serves as an intermediate cord, and the third cord 132c serves as a distal cord. In other embodiments, more or less than three of the cords 132a-132c can be included with the delivery device 120. The optional release pin 136 is slidably disposed within a separate lumen of the spindle 140 for reasons made clear below.

Figure 4A:
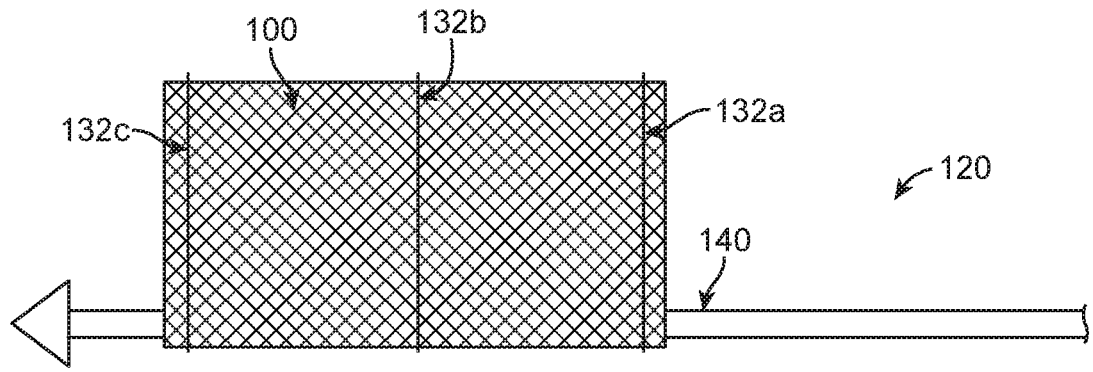
FIG. 4A is a simplified side view of a stented prosthetic heart valve and the delivery device of FIG. 2 in a tethered and expanded state.
Figure 4B:
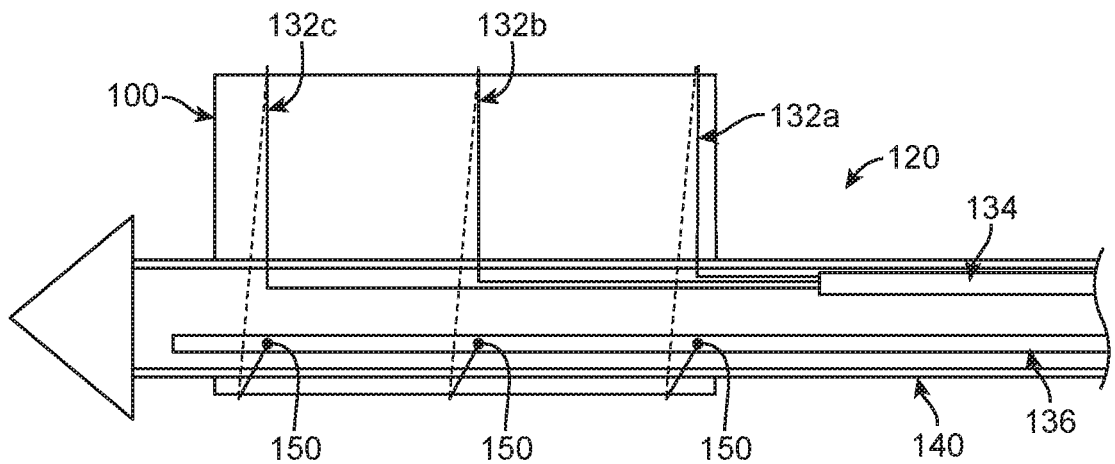
FIG. 4B is a simplified cross-sectional view of the arrangement of FIG. 4A.

FIGS. 4A and 4B illustrate, in simplified form, the stented prosthetic heart valve 100 as initially loaded to the delivery device 120. A length of each of the cords 132a-132c extending from the tension control rod 134 wraps about or engages a circumference of the prosthesis 100. The free end 150 of each of the cords 132a-132c is directed into the spindle 140 and brought into engagement with the release pin 136 (e.g., the free end 150 can from a loop that slidably receives the release pin 136). Alternatively, the release pin 136 can be omitted, with the free end 150 being routed through the inner shaft 130 and back to the handle assembly 138 (FIG. 2).

Figure 5A:
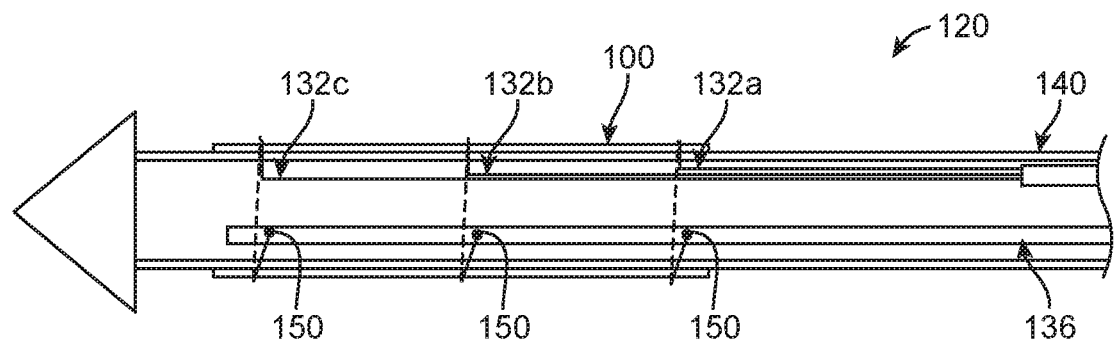
FIG. 5A is a simplified cross-sectional view of the components of FIG. 4A in a delivery state, including the stented prosthetic heart valve cinched to a compressed condition.
Figure 5B:
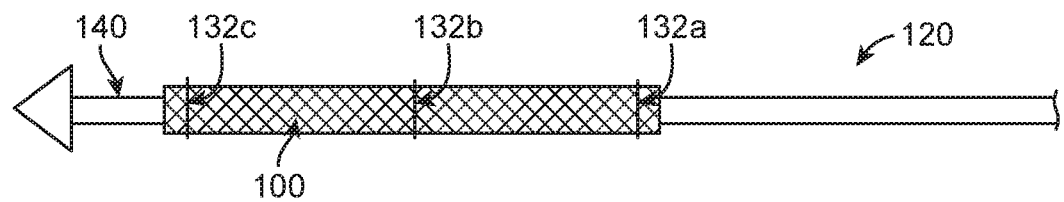
FIG. 5B is a simplified side view of the arrangement of FIG. 5A.
Figure 6:
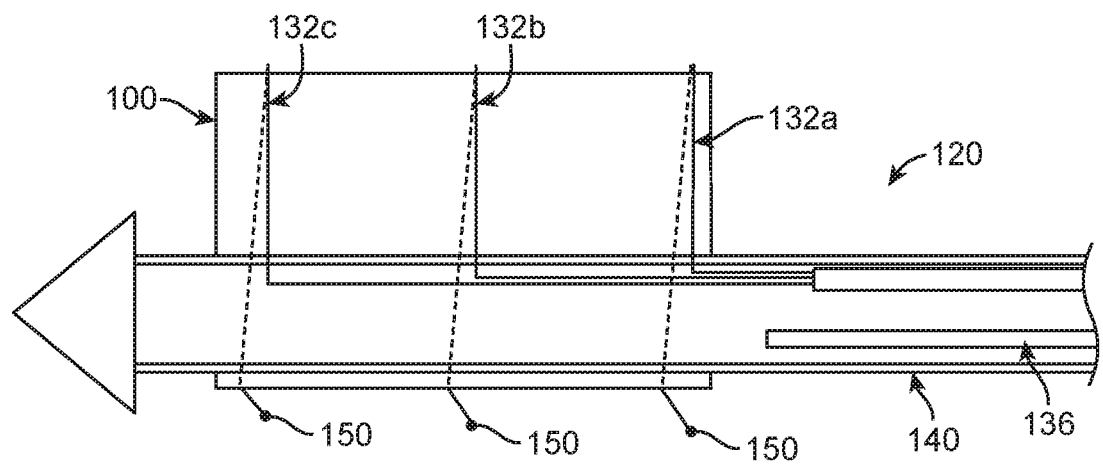
FIG. 6 is a simplified side view of the components of FIG. 4A and illustrating complete deployment of the stented prosthetic heart valve from the delivery device.

The stented prosthetic heart valve 100 can then be compressed or crimped on to the spindle 140 by proximally retracting the tension control rod 34 as reflected in the simplified view of FIGS. 5A and 5B. The release pin 136, and thus the free end 150 of each of the cords 132a-132c engaged therewith, remains stationary during proximal movement of the tension control rod 134. Thus, proximal retraction of the tension control rod 134 tensions the cords 132a-132c and shortens the length of each cord 132a-132c outside of the spindle 140, in turn forcing the prosthesis 100 to radially collapse or crimp. The delivery device 120 can then be used to deliver the prosthetic heart valve 100, in the loaded and compressed state of FIGS. 5A and 5B, to a target site via a patient's vasculature (or other percutaneous approach). Where provided, the optional outer sheath assembly 146 (FIG. 2) can be arranged to locate the capsule 148 (FIG. 2) over the compressed prosthetic heart valve 100 to minimize traumatic contact between the prosthesis 100 and bodily structures of the patient during delivery. Regardless, once the delivery device 120 has been manipulated to locate the prosthetic heart valve 100 at the targeted native valve site, the tension control rod 134 can be distally advanced relative to the spindle 140 back toward the arrangement of FIGS. 4A and 4B. Proximal advancement of the tension control rod 134 releases tension in the cords 132a-132c, allowing the prosthesis 100 to self-expand to or toward the normal, expanded condition reflected by the views. Relative to the order of steps, when returned to the arrangement of FIGS. 4A and 4B, the delivery device 120 and the prosthetic heart valve 100 are referred to throughout this disclosure as being in a tethered and expanded state (i.e., the prosthetic heart valve 100 has self-reverted to the normal, expanded condition, and remains connected or tethered to the delivery device 120 by the cords 132a-132c). The free end 150 of each of the cords 132a-132c is released from engagement with the release pin 136 as reflected by FIG. 6 (e.g., where the free ends 150 each are or include a loop slidably received over the release pin 136, the release pin 136 can be proximally retracted until removed from engagement with the free ends 150). The tension control rod 134 can then be proximally retracted, withdrawing the cords 132a-132c from the prosthetic heart valve 100 and into the inner shaft spindle 140. With the prosthesis 100 now fully released, the delivery device 120 can be withdrawn from the patient.

While the general construction and operation of the delivery device 120 (and similar designs) as described above is viable, opportunities for improvement remain. For example, in the tethered and expanded state of FIGS. 4A and 4B (i.e., tension in the cords 132a-132c has been lessened, allowing the prosthetic heart valve 100 to self-revert to or towards the normal, expanded condition while remaining tethered to the delivery device 120 by the cords 132a-132c), the prosthesis 100 may be laterally offset to one side of the spindle 140. Thus, the laterally offset spindle 140 may overtly contact or interfere with one or more of the leaflets 106 (FIG. 1A) provided with the prosthetic heart valve 100. Under circumstances where a clinician desires to evaluate or assess a functioning and/or location of the prosthesis 100 relative to the native valve anatomy prior to full release (e.g., assessment of valve hemodynamics and paravalvular leakage), the laterally offset spindle 140 causes or creates central regurgitation in the prosthetic heart valve 100 by preventing one or more of the valve leaflets 106 from functioning properly. Spindle-caused central regurgitation can render the assessment of valve hemodynamics exceedingly difficult. Embodiments of the present disclosure provide for different lateral arrangements of the prosthesis 100 relative to the spindle 140, including, for example, the spindle 140 being substantially centered (i.e., within 10% of a truly centered relationship) within the prosthesis 100 while in the expanded and tethered state, or held at one the commissures 108 (FIG. 1B) of the stented prosthetic heart valve 100.

For example, FIG. 7 illustrates portions of a delivery device 200 in accordance with principles of the present disclosure. The delivery device 200 is akin to the delivery device 120 (FIG. 2) as described above, and includes the inner shaft 130, the cords 132a-132c, the optional tension control rod 134, the handle assembly 138, and the outer sheath 146 (including the capsule 148) as described above. Further, the delivery device 200 includes release pins 202a-202c. In contrast to the single release pin 136 (FIG. 2) described above, with the delivery device 200, a plurality of the release pins 202a-202c are provided, one for each for each of the cords 132a-132c. Thus, while three of the release pins 202a-202c are shown, any other number, either greater or lesser, is equally acceptable, commensurate with the number of cords.

The release pins 202a-202c can be substantially identical in some embodiments, each formed of a shape memory material (e.g., Nitinol™). In the normal or set state shown, each of the release pins 202a-202c defines a proximal section 210, a bend section 212, and a distal section 214 (identified in FIG. 7 for the first release pin 202a). The release pins 202a-202c are approximately equidistantly spaced (e.g., within 10% of a truly equidistant spacing) from one another about a circumference of the inner shaft 130 as described below. The outer sheath 146 is slidably disposed over the release pins 202a-202c; in particular, the outer sheath 146 is arranged such that the capsule 148 selectively interfaces with the bend section 212 and the distal section 214 of each of the release pins 202a-202c with longitudinal movement of the outer sheath 146 relative to the inner shaft 130.

Figure 8A:
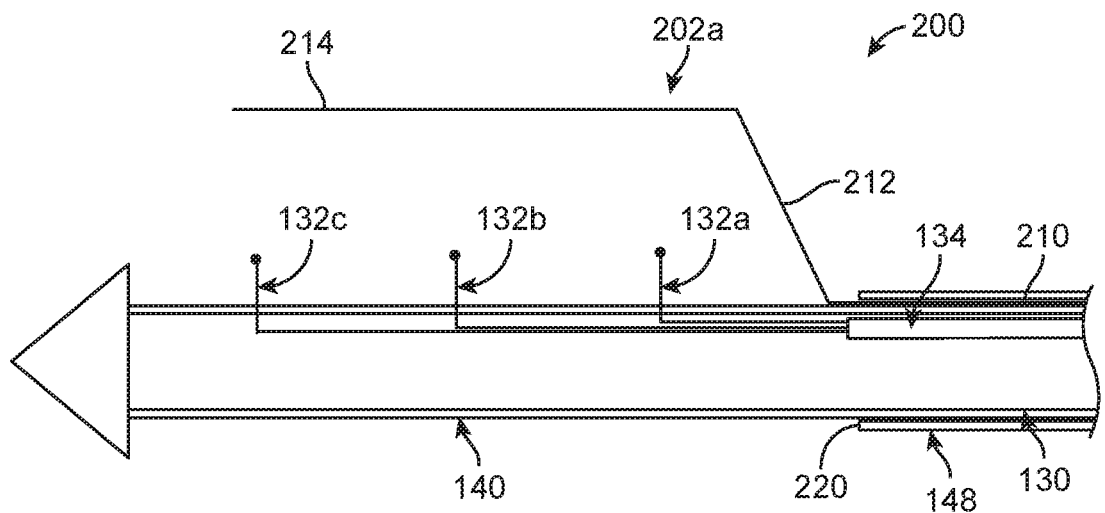
FIG. 8A is a simplified cross-sectional view of a portion of the delivery device of FIG. 7 upon final assembly and in a first arrangement.

FIG. 8A provides a simplified representation of a portion of the delivery device 200 upon final assembly, including arrangement of the first release pin 202a relative to the inner shaft 130. For ease of understanding, the second and third release pins 202b, 202c (FIG. 7) are omitted from the view. As with previous embodiments, the tension control rod 134 extends within a lumen of the inner shaft spindle 140, and the cords 132a-132c extend from the tension control rod 134. The proximal section 210 of the release pin 202a is connected to the inner shaft 130 in a manner permitting selective longitudinal movement of the release pin 202a relative to the inner shaft 130, as well as selective longitudinal locking of the release pin 202a relative to the inner shaft 130 (e.g., the release pin 202a can be selectively locked relative to the inner shaft 130 at the handle assembly 138 (FIG. 7)). In this regard, the proximal section 210 can be disposed along an outer surface of the inner shaft 130 as shown; alternatively, the proximal section 210 can be located within a lumen of the inner shaft 130 or embedded within a wall thickness of the inner shaft 130. The capsule 148 is slidably disposed over the release pin 202a.

Figure 8B:
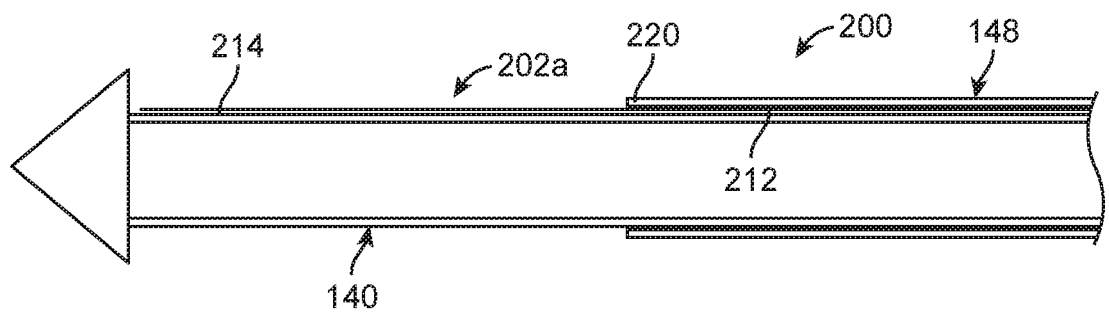
FIG. 8B is a simplified cross-section view of the portion of FIG. 8A and in a second arrangement.

In the expanded arrangement of FIG. 8A, a distal end 220 of the capsule 148 is proximal the bend section 212 of the release pin 202a. Thus, the release pin 202a freely self-assumes the normal, bent shape as shown in which the bend section 212 projects radially from the inner shaft spindle 140, locating the distal section 214 at a radial or lateral spacing from the spindle 140. When the capsule 148 is distally advanced over at least a portion of the bend section 212 as in FIG. 8B, the capsule 148 forces or deflects the release pin 202a to or toward a more straightened shape, biasing the bend section 212 toward the inner shaft spindle 140. When the capsule 148 is subsequently proximally retracted relative to the release pin 202a, the release pin 202a self-reverts back to the normal, bent shape (i.e., returns to the arrangement of FIG. 8A).

Figure 8C:
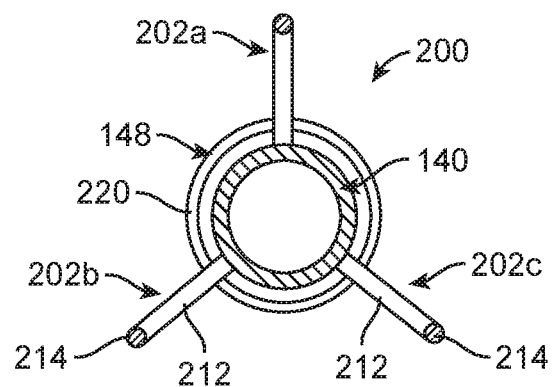
FIG. 8C is a simplified lateral cross-sectional view of a portion of the delivery device of FIG. 7 in the arrangement of FIG. 8A.

The simplified lateral cross-sectional view of FIG. 8C illustrates the approximately equidistant spacing of the release pins 202a-202c relative to a circumference of the spindle 140. As a point of reference, in the view of FIG. 8C, the distal end 220 of the capsule 148 is proximal the bend section 212 of each of the release pins 202a-202c such that the release pins 202a-202c self-assume the bent shape shown, including the distal sections 214 being laterally spaced from the spindle 140.

Figure 9A:
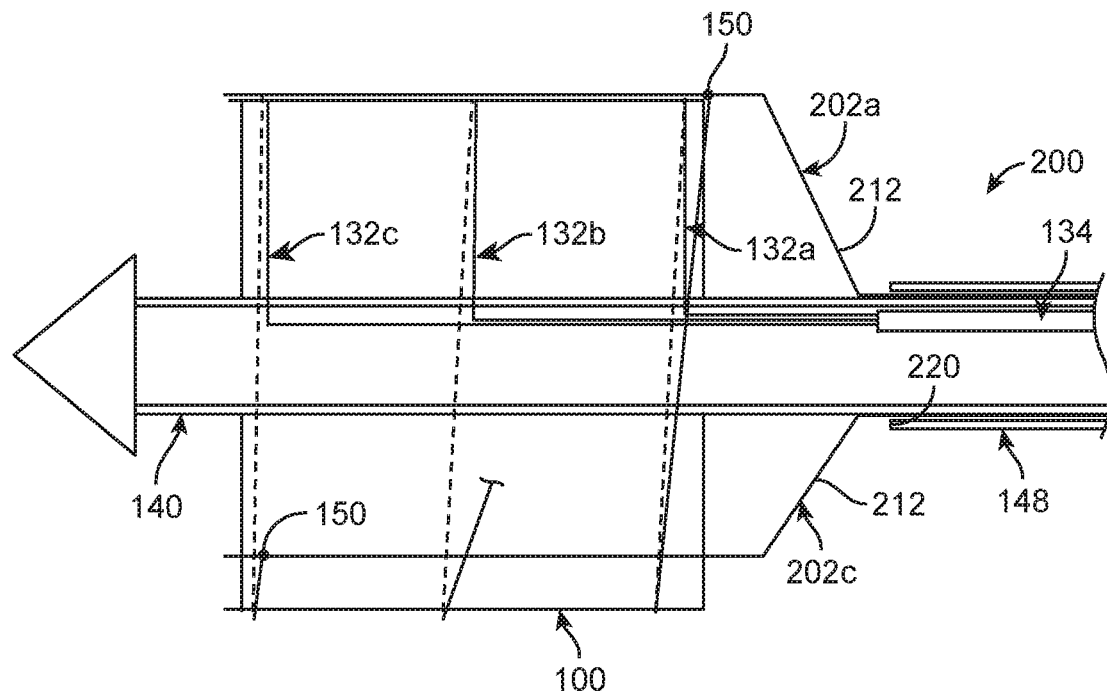
FIG. 9A is a simplified cross-sectional side view of a stented prosthetic heart valve and the delivery device of FIG. 7 in a tethered and expanded state.
Figure 9B:
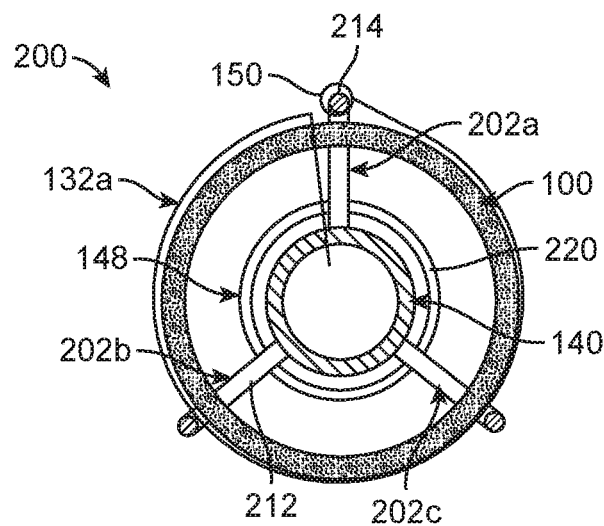
FIG. 9B is a simplified lateral cross-sectional view of the arrangement of FIG. 9A.

A stented prosthetic heart valve can be coupled or loaded to, and subsequently deployed from, the delivery device 200 in manners akin to the descriptions above. For example, FIGS. 9A and 9B are simplified views of the prosthetic heart valve 100 initially loaded to the delivery device 200. As a point of reference, in the simplified longitudinal view of FIG. 9A, the inner shaft 130, including the spindle 140, is shown in cross-section and the second release pin 202b is hidden. The first-third cords 132a-132c extend from the tension control rod 134, through a respective hole or port (not shown) in the spindle 140 and about (or along) a circumference of the prosthesis 100. The first cord 132a is wound or wrapped along the circumference, and the corresponding free end 150 is releasably coupled to the first release pin 202a. The simplified lateral cross-sectional view of FIG. 9B reflects this arrangement, and shows the free end 150 of the first cord 132a optionally forming or including a loop that is slidably disposed over the first release pin 202a. The second cord 132b is wrapped about a circumference of the prosthetic heart valve 100 and releasably connected to the second release pin 202b; the third cord 132c is wrapped about a circumference of the prosthetic heart valve 100 and releasably connected to the third release pin 202c.

Figure 10A:
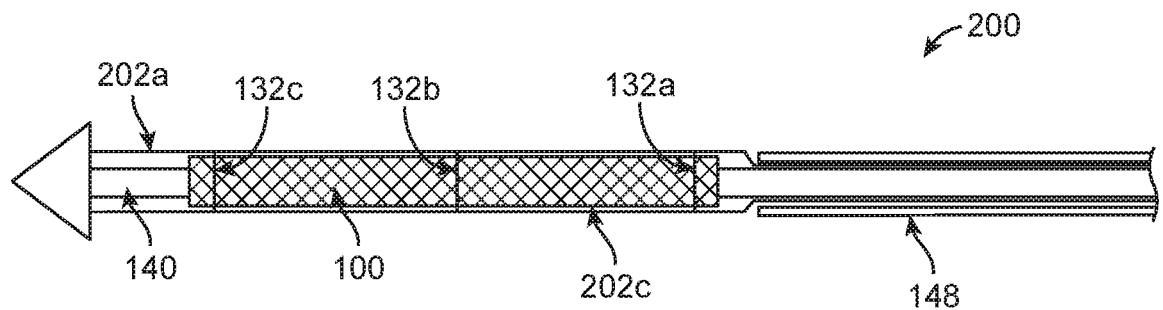
FIG. 10A is a simplified side view of the components of FIG. 9A in a delivery state, including the stented prosthetic heart valve cinched to a compressed condition.

In the arrangement of FIGS. 9A and 9B, the distal end 220 of the capsule 148 is proximal the bend section 212 of each of the release pins 202a-202c, allowing the release pins 202a-202c to freely assume the bent or expanded shape shown. The prosthetic heart valve 100 is subsequently compressed or collapsed onto the spindle 140 by proximally retracting the tension control rod 134 relative to the spindle 140 as describe above. Further, and as shown in FIG. 10A, the capsule 148 is distally advanced relative to the spindle 140 and the release pins 202a-202c, forcing the release pins 202a-202c to or toward a more straightened shape. As a point of reference, in the simplified representation of FIG. 10A, the second release pin 202b is hidden; further, the first and third release pins 202a, 202c are represented as being approximately 180 degrees apart for ease of illustration, it being understood that with embodiments in which three of the release pins 202a-202c are provided, the first and third release pins 202a, 202c will be circumferentially spaced by approximately 120 degrees.

Figure 10B:
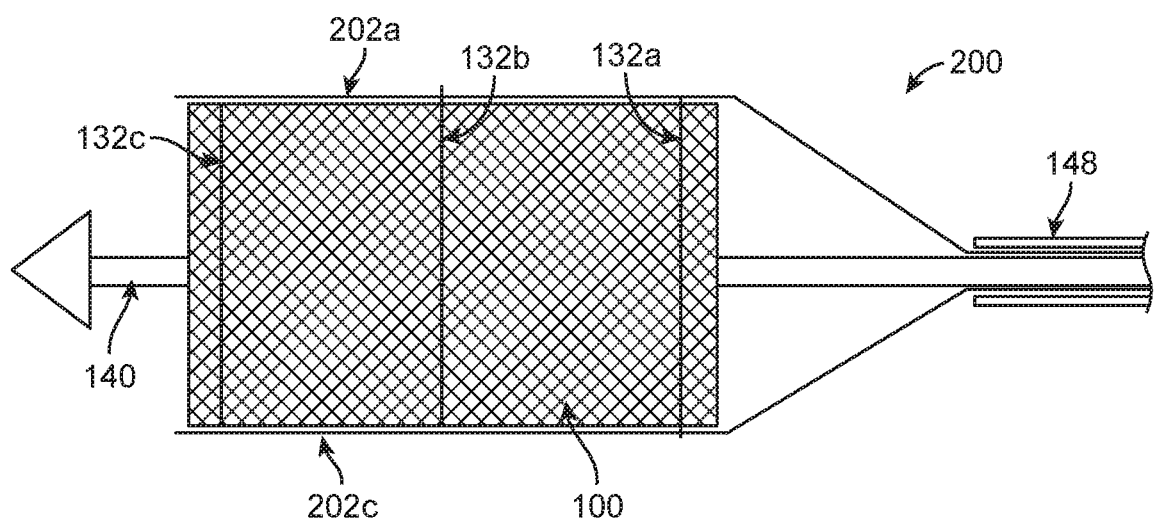
FIG. 10B is a simplified side view of the tethered and expanded state of FIG. 9A.

In the delivery state of FIG. 10A (e.g., the prosthesis 100 has been crimped and the release pins 202a-202c rendered relatively straight), the delivery device 200 can be manipulated to deliver the compressed prosthesis 100 to a targeted native valve. The capsule 148 is proximally retracted, and tension in the cords 132a-132c is then released as described above. As the stented prosthetic heart valve 100 self-reverts toward the normal, expanded condition, the release pins 202a-202c self-revert toward the normal, bent shape as shown in FIG. 10B. With this arrangement, then, the release pins 202a-202c keep the prosthesis 100 substantially centered relative to the spindle 140 during deployment. As a point of reference, the tethered and expanded state of the stented prosthetic heart valve 100 relative to the delivery device 200 is also reflected by the views of FIGS. 9A and 9B. With this substantially centered relationship, the expanded prosthesis 100 can be evaluated (e.g., hemodynamic check) with minimal or no interference by the spindle 140 (e.g., leaflets of the prosthesis will coapt on to the spindle 140). Once the clinician is satisfied with an anatomical location and functioning of the expanded and tethered prosthetic heart valve 100, the release pins 202a-202c are de-coupled from the corresponding cord 132a-132c (e.g., the release pins 202a-202c are proximally retracted), allowing the cords 132a-132c to be removed from engagement with the prosthesis 100 as described above.

Figure 11:
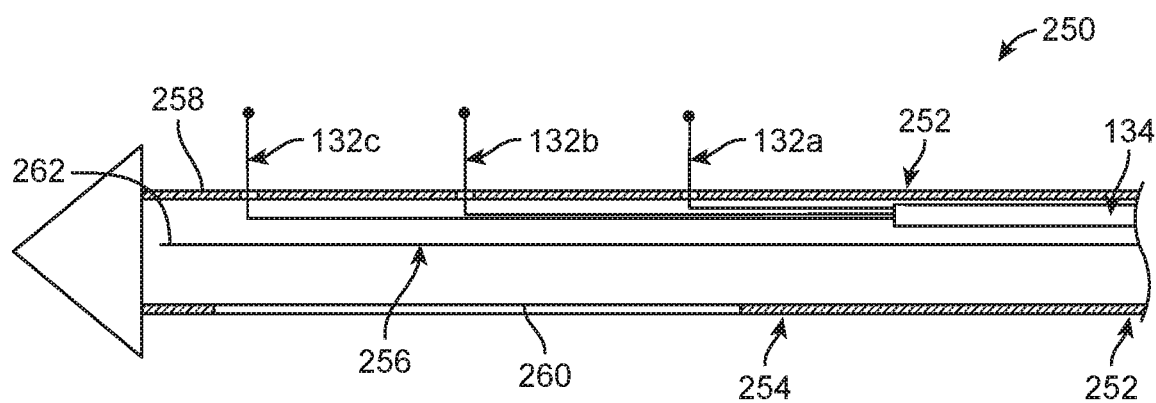
FIG. 11 is a simplified cross-sectional view of a portion of another delivery device in accordance with principles of the present disclosure.

Portions of another delivery device 250 in accordance with principles of the present disclosure are shown in simplified form in FIG. 11. The delivery device 250 is akin to previous embodiments and includes an inner shaft 252 forming or carrying a spindle 254, the plurality of cords 132a-132c, the optional tension control rod 134, a release pin 256, and a handle assembly (not shown, but akin to the handle assembly 38 (FIG. 2) described above). The inner shaft 252, including the spindle 254, can assume any of the forms described above with respect to the inner shaft 130 (FIG. 2) and the spindle 140 (FIG. 2). With the embodiment of FIG. 11, in addition to forming holes or ports (one of which is identified at 258 in FIG. 11) sized to slidably receive respective ones of the cords 132a-132c, the spindle 140 defines a slot 260 configured to permit selective passage of a portion of the release pin 256 as described below. In this regard, the spindle 254 forms an individual lumen or "release pin lumen" (not shown in FIG. 11 for ease of illustration) within which the release pin 256 is slidably received, with the slot 260 being open to the release pin lumen. For ease of illustration, FIG. 11 depicts the slot 260 as being opposite the ports 258; in other embodiments, the slot 260 can be formed circumferentially adjacent the ports 258. The release pin 256 naturally assumes the relatively straight, linear shape shown, but is sufficiently robust to resiliently or non-deformably deflect when subjected to external forces. The release pin 256 terminates at a distal end 262.

Figure 12A:
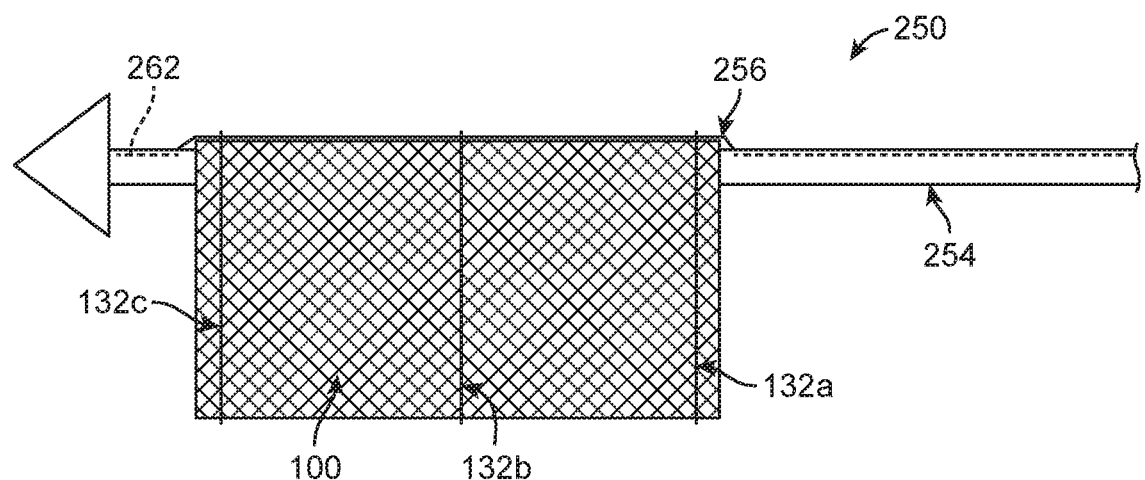
FIG. 12A is a simplified side view of a stented prosthetic heart valve and the delivery device of FIG. 11 in a tethered and expanded state.
Figure 12B:
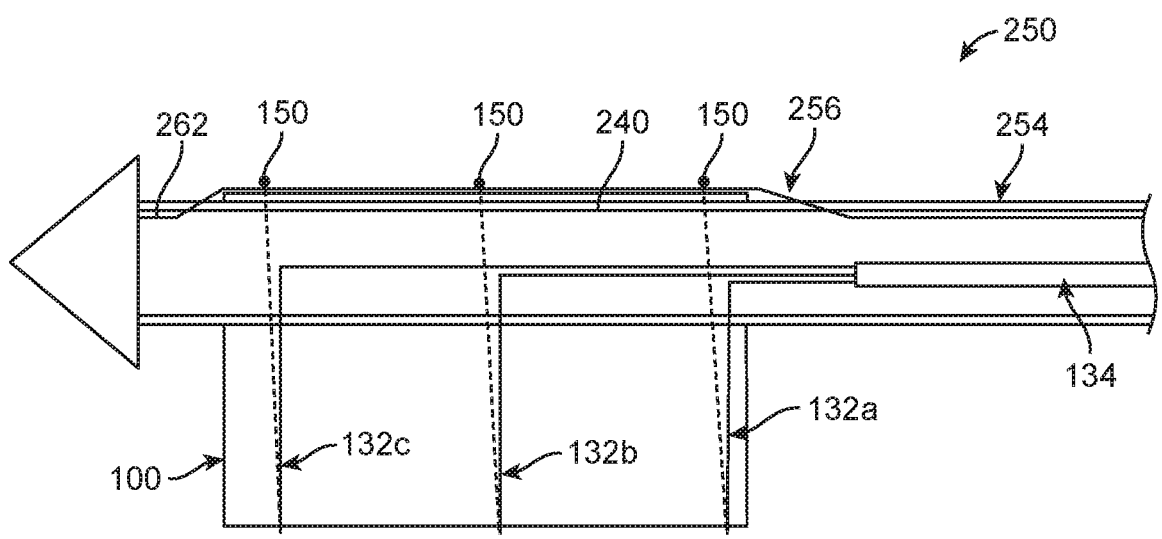
FIG. 12B is a simplified cross-sectional view of the arrangement of FIG. 12A.
Figure 12C:
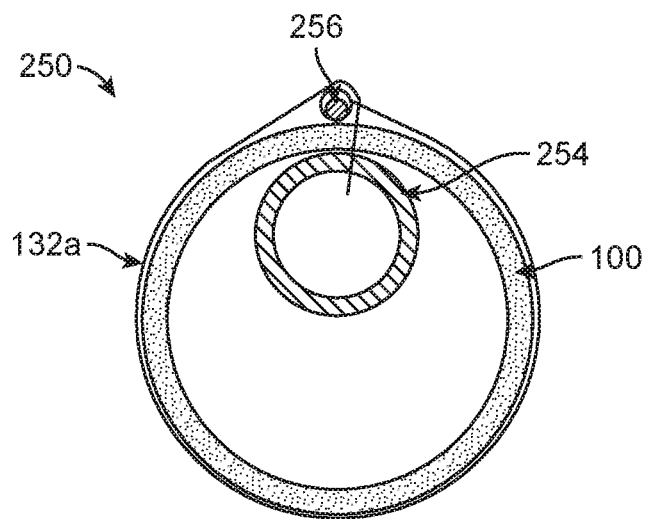
FIG. 12C is a simplified lateral cross-sectional view of the arrangement of FIG. 12A.

A stented prosthetic heart valve can be coupled or loaded to, and subsequently deployed from, the delivery device 250 in manners akin to the descriptions above. For example, FIGS. 12A and 12B are simplified views of the prosthetic heart valve 100 initially loaded to the delivery device 250. The release pin 256 is arranged to extend outwardly from the spindle 254 proximal the prosthesis 100 via the slot 260, along an exterior of the prosthesis 100, and back into the spindle 254 distal the prosthesis 100 via the slot 260. A rotational arrangement of the stented prosthetic heart valve 100 relative to the release pin 256 can be selected to align structural features of the prosthesis 100 with the release pin 256. For example, one of the commissures 108 (FIG. 1B) of the stented prosthetic heart valve 100 can be aligned with the release pin 256 for reasons made clear below. The distal end 262 of the release pin 256 is lodged within the spindle 254 such that the release pin 256 presses or forces the prosthetic heart valve 100 toward or onto the spindle 254. As with previous embodiments, the first-third cords 132a-132c extend from the tension control rod 134, through a respective hole or port (not shown) in the spindle 254 and about (or along) a circumference of the prosthesis 100. The corresponding free end 150 of each of the cords 132a-132c is releasably coupled to the release pin 256. The simplified lateral cross-sectional view of FIG. 12C reflects this arrangement, and shows the free end 150 of the first cord 132a as optionally forming or including a loop that is slidably disposed over the release pin 256. FIG. 12C further illustrates an optional arrangement in which winding of the first cord 132a about the stented prosthetic heart valve 100 includes routing the first cord 132a over or around the release pin 256 (e.g., relative to the orientation of FIG. 12C, the first cord 132a is routed from the spindle 254 through the prosthesis 100 at a first side of the release pin 256 and then over the release pin 256 as the first cord 132a is wrapped about the prosthesis 100 in the counter-clockwise direction). In other arrangements, the first cord 132a is not routed over or around the release pin 256.

Figure 13:
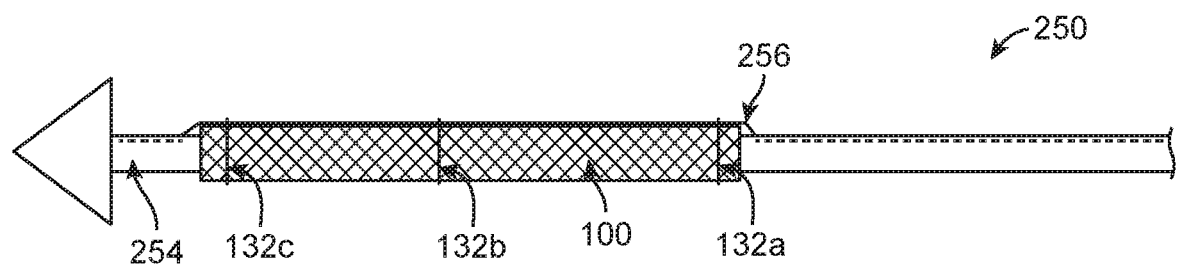
FIG. 13 is a simplified side view of the components of FIG. 12A in a delivery state, including the stented prosthetic heart valve cinched to a compressed condition.

The prosthetic heart valve 100 is subsequently compressed or cinched onto the spindle 254 by proximally retracting the tension control rod 134 relative to the spindle 254 as describe above. In the delivery state of FIG. 13 (e.g., the prosthesis 100 is collapsed and the release pin 256 extends along an exterior of the prosthesis 100), the delivery device 250 can be manipulated to deliver the cinched prosthesis 100 to a targeted native valve. Tension in the cords 132a-132c can then be released to deploy the prosthesis 100 as described above. As the stented prosthetic heart valve 100 self-reverts toward the normal, expanded condition, the release pin 256 maintains the prosthesis 100 against the spindle 254 (reflected by the views of FIGS. 12A-12C). With embodiments in which the release pin 256 is aligned with one of the commissures 108 (FIG. 1B) of the stented prosthetic heart valve 100, the spindle 254 is effectively locked at the commissure 108, facilitating meaningful evaluation of the prosthesis 100 in the tethered and expanded state. Once the clinician is satisfied with an anatomical location and functioning of the expanded and tethered prosthetic heart valve 100, the release pin 256 is uncoupled from the cords 132a-132c (e.g., the release pin 256 is proximally retracted), allowing the cords 132a-132c to be removed from engagement with the prosthesis 100 as described above.

Figure 14A:
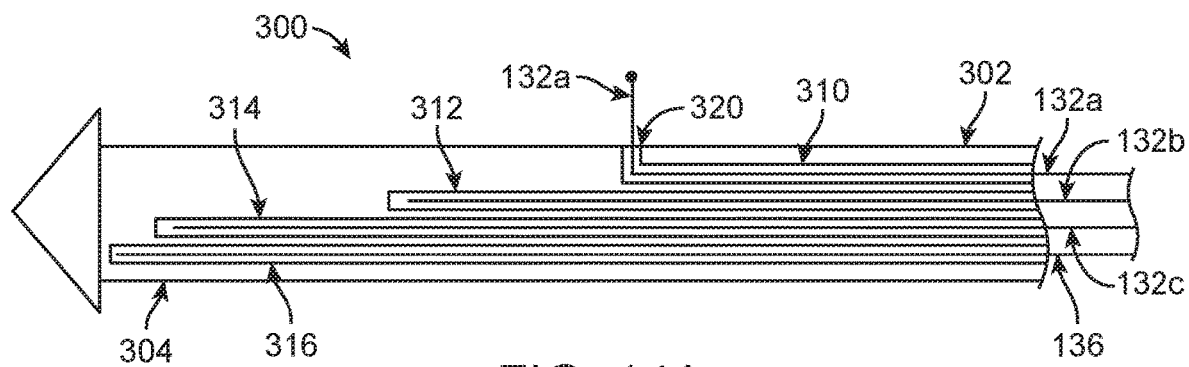
FIG. 14A is a simplified cross-sectional view of a portion of another delivery device in accordance with principles of the present disclosure.

Portions of another embodiment delivery device 300 in accordance with principles of the present disclosure are shown in simplified form in FIG. 14A. The delivery device 300 is akin to previous embodiments and includes an inner shaft 302 forming or carrying a spindle 304, the plurality of cords 132a-132c, the optional release pin 136, and a handle assembly (not shown, but akin to the handle assembly 138 (FIG. 2) described above).

Figure 14B:
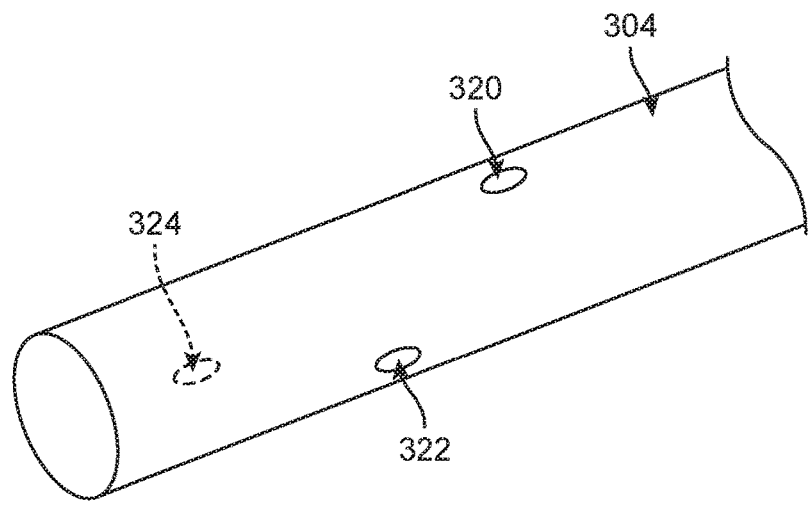
FIG. 14B is a simplified perspective view of a spindle useful with the delivery device of FIG. 14A.

The inner shaft 302, including the spindle 304, can assume any of the forms described above with respect to the inner shaft 130 (FIG. 2) and the spindle 140 (FIG. 2). With the embodiment of FIG. 14A, the inner shaft 302 and the spindle 304 form separate lumens for each of the cords 132a-132c and for the release pin 136 (where provided). The lumens are schematically reflected in FIG. 14A and include a first lumen 310 within which the first cord 132a is slidably received, a second lumen 312 within which the second cord 132b is slidably received, a third lumen 314 within which the third cord 132c is slidably received, and a fourth lumen 316 within which the release pin 136 is slidably received. One or more additional lumens (e.g., a guide wire lumen) can be further provided. Each of the cord lumens 310-314 is open to an exterior of the spindle 304 at a hole or port. For example, FIG. 14A illustrates the first lumen 310 terminating at a first lumen hole or opening 320 through which the first cord 132a can pass or extend from the first lumen 310 to an exterior of the spindle 304. The second and third lumens 312, 314 are offset from the first lumen 310 and each other, and the holes associated with the cord lumens 310-314 are longitudinally and circumferentially offset from one another. FIG. 14B schematically reflects this arrangement. With reference between FIGS. 14A and 14B, the second lumen 312 terminates at and is open to a second lumen hole or opening 322 that is longitudinally spaced from the first lumen hole 320 in the distal direction, and is circumferentially offset from the first lumen hole 320. The third lumen 314 terminates at and is open to a third lumen hole or opening 324 that is longitudinally spaced from the second lumen hole 322 in the distal direction, and is circumferentially offset from the first and second lumen holes 320, 322.

Figure 14C:
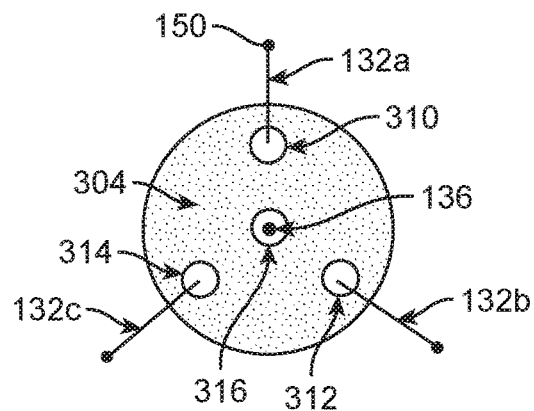
FIG. 14C is a simplified lateral cross-sectional view of the delivery device of FIG. 14A.

The circumferential offset of the lumen holes 320-324 establishes an approximately equidistantly circumferential spacing in some embodiments. For example, a circumferential offset between the lumen holes 320-324 can be approximately 120 degrees (plus or minus 10 degrees). With additional reference to FIG. 14C, the circumferential location of the lumen holes 320-324 generates a distinct connection or extension angle for each of the cords 132a-132c, with the cords 132a-132c being circumferentially offset from one another. In one embodiments, and relative to the orientation of FIG. 14C, the first cord 132a can be viewed as being at a connection location of 0 degrees, the second cord 132b at 120 degrees and the third cord 132c at 240 degrees. Where more or less than three of the cords 132a-132c are included (and thus a corresponding number of cord lumens), a corresponding circumferential offset can be effectuated by the lumen holes to establish the approximately equidistant circumferential spacing of the cords. As a point of reference, FIG. 14C further reflects the release pin 136 within the fourth lumen 316. The fourth lumen 316 can be open to an exterior of the spindle 304 for receiving the free end 150 of each of the cords 132a-132c in various manners, such as by a slot (not shown). In other embodiments, the release pin 136 can be omitted, with the free end 150 of each of the cords 132a-132c being threaded back to the handle assembly 38 (FIG. 2).

Figure 15A:
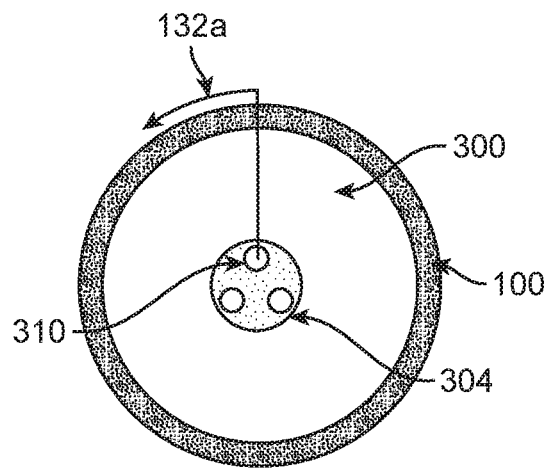
FIGS. 15A-15C illustrating routing of a cord of the delivery device of FIG. 14A to a stented prosthetic heart valve.
Figure 15B:
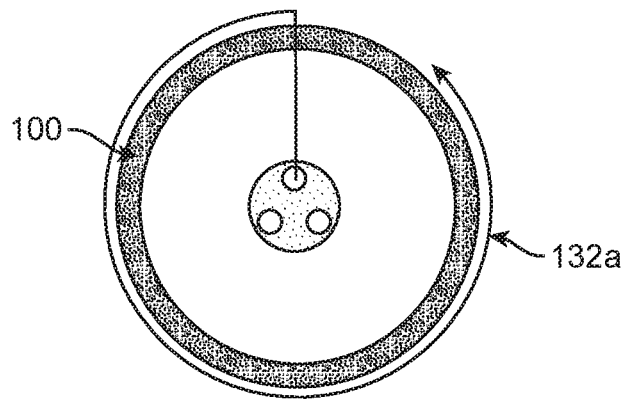
Figure 15C:
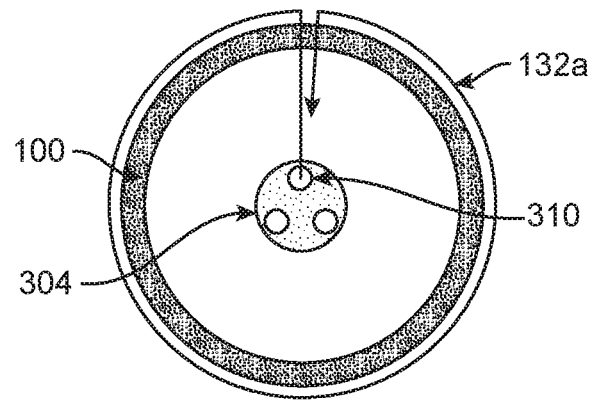

A stented prosthetic heart valve can be coupled or loaded to, and subsequently deployed from, the delivery device 300 in manners akin to the descriptions above, including each of the cords 132a-132c extending from the corresponding lumen hole 320-324 and wrapped about or along a circumference of the prosthesis. For example, FIGS. 15A-15C illustrate, in simplified form, connection of the first cord 132a to the stented prosthetic heart valve 100. As shown in FIG. 15A, the first cord 132a is extended from the first cord lumen 310 and the spindle 304 to the prosthesis 100, and then wrapped along the prosthesis 100 in a direction generally indicated by an arrowhead. Wrapping of the first cord 132a about the stented prosthetic heart valve 100 continues as in FIG. 15B (with the direction of extension of the first cord 132a again indicated by an arrowhead). Once the first cord 132a has been wrapped at least approximately a full revolution along the prosthesis 100, the first cord 132a is directed back to the spindle 304 as in FIG. 15C. The first cord 132a can then be connected with the release pin 136 (FIG. 14C) as with other embodiments, or can be routed back through the first cord lumen 310.

Figure 16A:
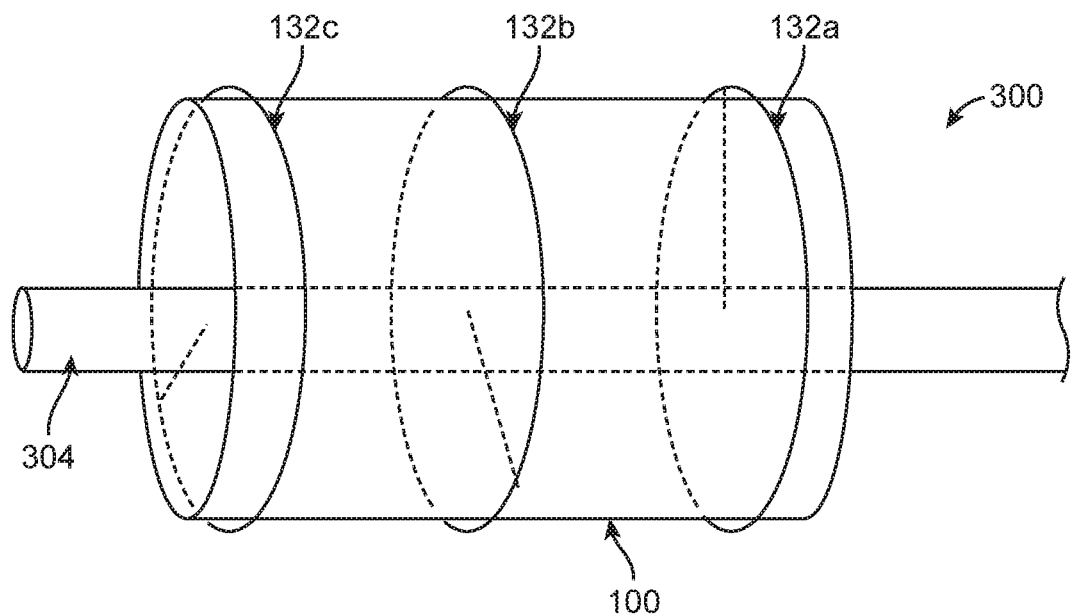
FIG. 16A schematically illustrates routing of three cords of the delivery device of FIG. 14A to a stented prosthetic heart valve.
Figure 16B:
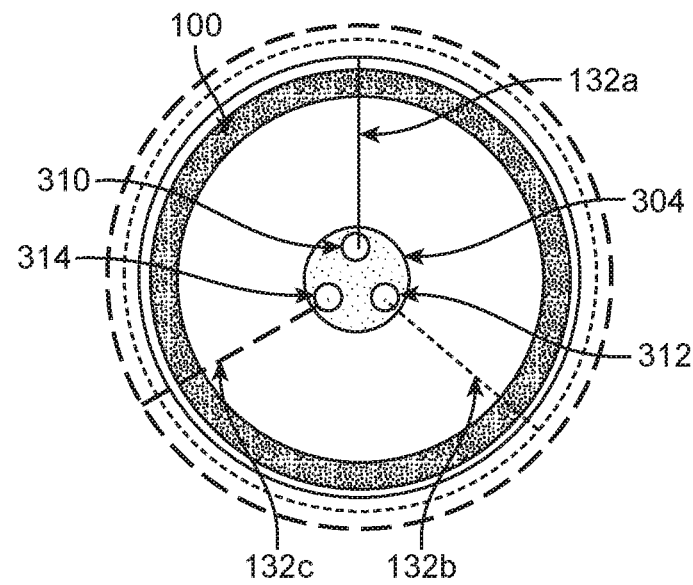
FIG. 16B is a simplified lateral cross-sectional view of a stented prosthetic heart valve and the delivery device of FIG. 14A in a tethered and expanded state.

The second and third cords 132b, 132c are similarly connected to, or wrapped about, the prosthesis 100 as illustrated in simplified form in FIG. 16A. As shown, the cords 132a-132c are longitudinally spaced from one another along a length of the stented prosthetic heart valve 100. Further, the locations of connection between the spindle 304 and the prosthesis 100 established by each of the cords 132a-132c are circumferentially offset from one another, for example by 120 degrees. FIG. 16B further reflects this circumferential offset of the cord connection angles. For ease of understanding, in the view of FIG. 16B, the first cord 132a is drawn with a solid line, the second cord 132b is drawn with short dashes, and the third cord 132c is drawn with a long dashes.

Figure 17A:
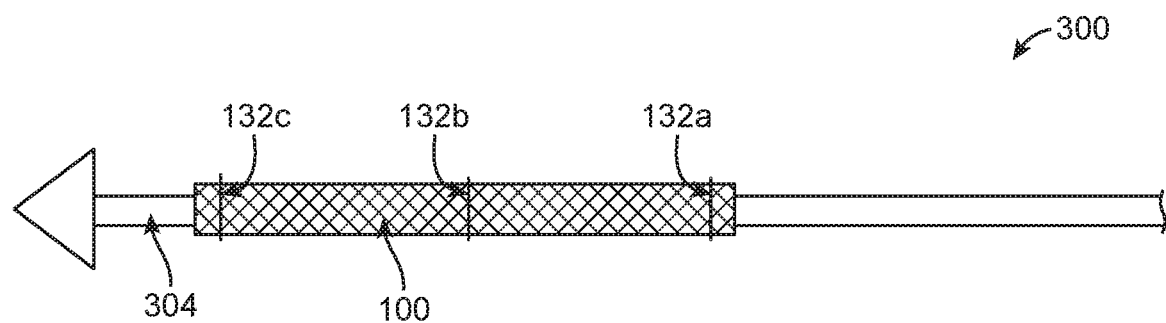
FIG. 17A is a simplified side view of the components of FIG. 16B in a delivery state, including the stented prosthetic heart valve cinched to a compressed condition.
Figure 17B:
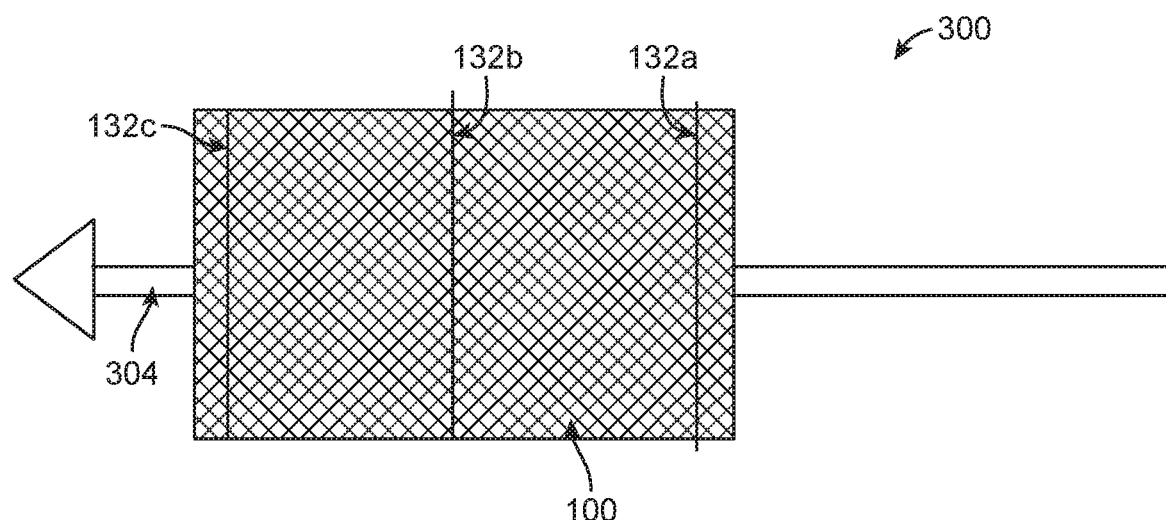
FIG. 17B is a simplified side view of the tethered and expanded state of FIG. 16B.

The prosthetic heart valve 100 is subsequently compressed or crimped onto the spindle 304 by tensioning or proximally retracting the cords 132a-132c. Though not shown, each of the cords 132a-132c can be connected to a corresponding tension control rod that is operated to apply tension; alternatively, the cords 132a-132c can be threaded to the handle assembly 138 (FIG. 2) that is actuated to generate tension. In the delivery state of FIG. 17A (e.g., the prosthesis 100 is collapsed or crimped onto the spindle 304 by the cords 132a-132c), the delivery device 300 can be manipulated to deliver the compressed prosthesis 100 to a targeted native valve. Tension in the cords 132a-132c can then be released to deploy the prosthesis 100 as described above. As the stented prosthetic heart valve 100 self-reverts toward the normal, expanded condition, the circumferentially spaced cords 132a-132c provide equal tension at equidistantly spaced locations between the prosthesis 100 and the spindle 304, thus maintaining the spindle 304 in the center of the prosthetic heart valve 100 as reflected by FIG. 17B. As a point of reference, the tethered and expanded state of the stented prosthetic heart valve 100 relative to the delivery device 300 is also reflected by the views of FIGS. 16A and 16B. With this substantially centered relationship, the expanded prosthesis 100 can be evaluated (e.g., hemodynamic check) with minimal or no interference by the spindle 304. Once the clinician is satisfied with an anatomical location and functioning of the expanded and tethered prosthetic heart valve 100, the cords 132a-132c are removed from engagement with the prosthesis 100 as described above.

Figure 18:
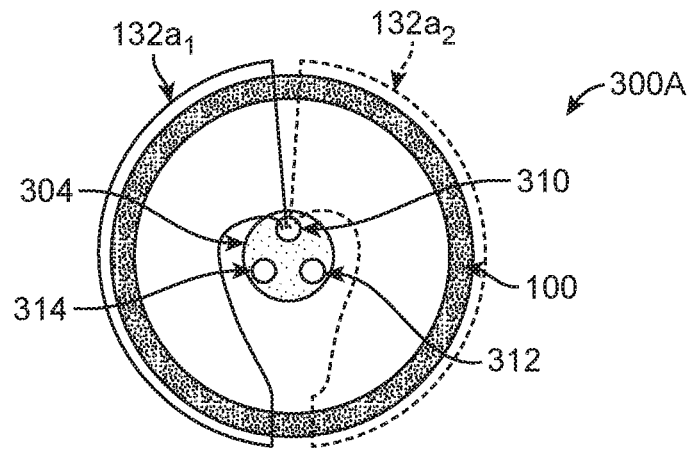
FIG. 18 is a simplified lateral cross-sectional view of a portion of another delivery device in accordance with principles of the present disclosure connected to a stented prosthetic heart valve in a tethered and expanded state.

Portions of a related embodiment delivery device 300A are shown in simplified form in FIG. 18 relative to a loaded stented prosthetic heart valve 100. In general terms, the delivery device 300A can be highly akin to the delivery device 300 (FIG. 14A) described above, including the inner shaft spindle 304 forming the first-third cord lumens 310-314 that are each open to an exterior of the spindle 304 at longitudinally and circumferentially spaced openings 320-324 (FIG. 14B). The delivery device 300A also includes a plurality of cords akin to the above descriptions. With the embodiment of FIG. 18, however, two cords are provided in each of the cord lumens 310-314. For ease of understanding, only first and second cords 132ai, 132a2 (within the first cord lumen 310) are illustrated in FIG. 18, it being understood that two additional cords will be provided within the second cord lumen 312 and another two additional cords will be provided within the third cord lumen 314. Further, the first cord 132ai is represented by a solid line, whereas the second cord 132a2 is represented by a dashed line for ease of understanding. The first and second cords 132ai, 132a2 each extend from the first cord lumen 310 through the opening 320 (FIG. 14B) to the prosthesis 100, commensurate with the descriptions above. The first and second cords 132ai, 132a2 then wind or extend in opposite directions along approximately one-half of a circumference of the stented prosthetic heart valve 100, and return to the spindle 304.

Figure 19A:
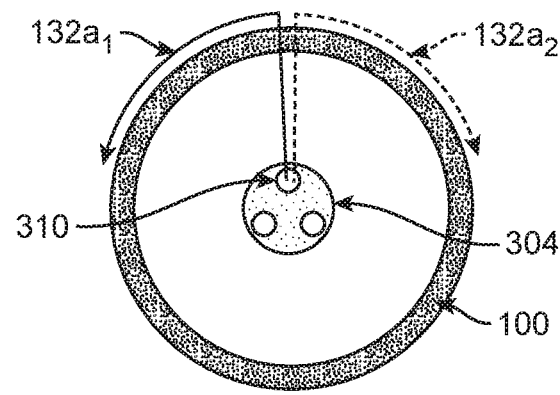
FIGS. 19A and 19B schematically illustrate routing of two cords of the delivery device of FIG. 18 to the stented prosthetic heart valve.
Figure 19B:
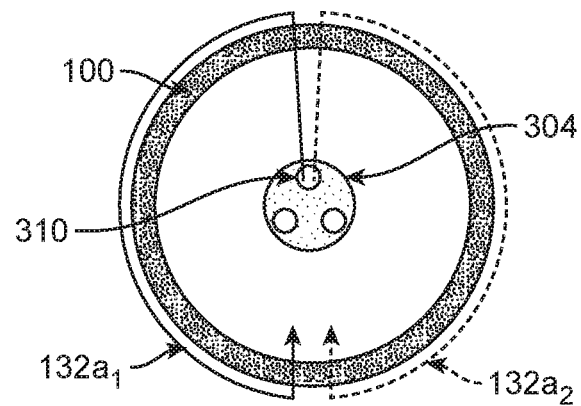

By way of further explanation, FIG. 19A depicts initial threading of the cords 132ai, 132a2 from the first cord lumen 310 to the prosthesis 100, and then partially along the prosthesis 100 in opposite directions. Winding or threading directions of the cords 132ai, 132a2 are identified by arrowheads. Once wrapped approximately one-half the circumference of the stented prosthetic heart valve 100, the cords 132ai, 132a2 are then extend back toward the spindle 304 as reflected by FIG. 19B.

Returning to FIG. 18, the two cords (not shown) associated with the second cord lumen 312 and the two cords (not shown) associated with the third cord lumen 314 are similarly connected to the prosthesis 100 (e.g., highly akin to the cord connection pattern illustrated in FIG. 16A, except that each of the cords 132a-132c of FIG. 16A are replaced by two cords, each connected to approximately one-half the circumference of the prosthesis 100). The delivery device 300A can then be operated in accordance with the descriptions above to collapse or crimp the prosthesis 100 for delivery to a target site by tensioning the cords. Tension in the cords is then lessened to allow the stented prosthetic heart valve 100 to self-revert toward the normal, expanded condition. In this regard, each half-circumference cord (e.g., the cords 132ai, 132a2) will create tension between the prosthesis 100 and the spindle 304 in substantially equal proportions, providing more stable centering of the spindle 304 relative to the prosthesis 100 in the expanded and tethered state.

Figure 20:
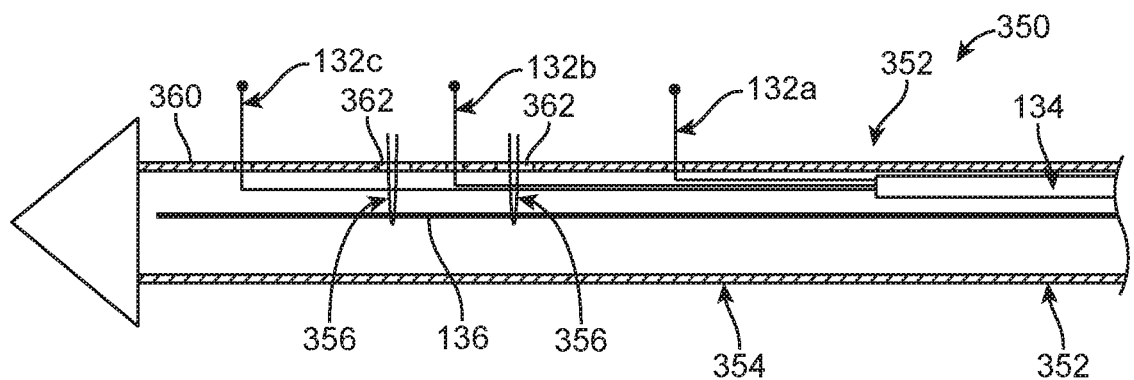
FIG. 20 is a simplified cross-sectional view of a portion of another delivery device in accordance with principles of the present disclosure.

Portions of another embodiment delivery device 350 in accordance with principles of the present disclosure are shown in simplified form in FIG. 20. The delivery device 350 is akin to previous embodiments and includes an inner shaft 352 forming or carrying a spindle 354, the plurality of cords 132a-132c, the optional tension control rod 134, the release pin 136, and a handle assembly (not shown, but akin to the handle assembly 138 (FIG. 2) described above). In addition, the delivery device 350 includes one or more connectors 356 for selectively connecting the release pin 136 to a selected location of a stented prosthetic heart valve (not shown) as described below.

The inner shaft 352 and the spindle 354 can assume any of the forms described elsewhere in the present disclosure, with the spindle 354 forming holes (one of which is labelled at 360) through which respective ones of the cords 132a-132c can be routed to and from an exterior of the spindle 354. The spindle 354 further defines one or more ports 362 through which respective ones of the connectors 356 can enter a lumen of the spindle 354.

The connector(s) 356 can assume various forms appropriate for coupling to a frame of a stented prosthetic heart valve (not shown) and to the release pin 136. For example, the connector(s) 356 can be a short wire, suture, etc., that can be threaded to the prosthesis frame and then tied to form a loop. The release pin 136, in turn, is slidably received within the loop. Other connection formats are also acceptable.

Figure 21A:
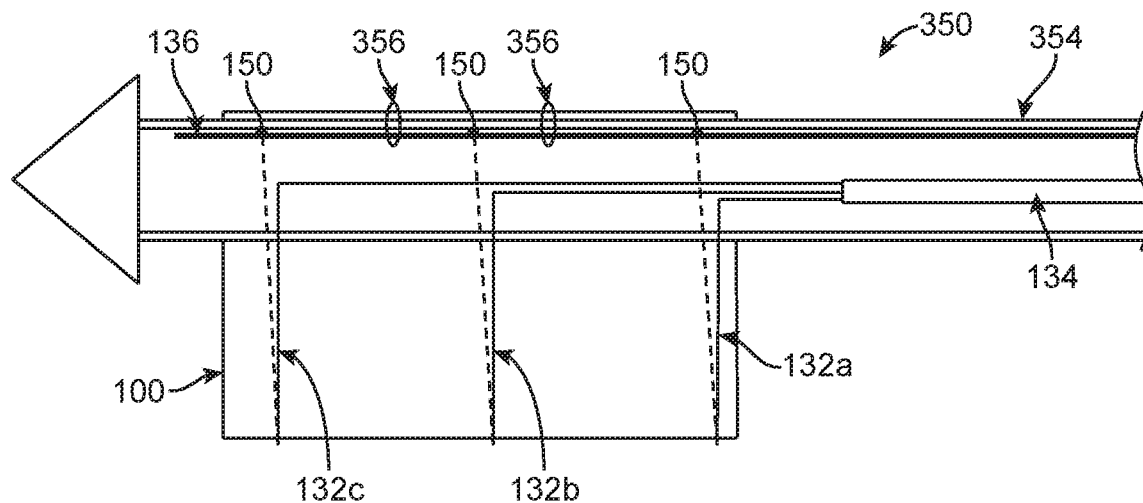
FIG. 21A is a simplified cross-sectional view of a stented prosthetic heart valve and the delivery device of FIG. 20 in a tethered and expanded state.

A stented prosthetic heart valve can be coupled or loaded to, and subsequently deployed from, the delivery device 350 in manners akin to the descriptions above. For example, FIG. 21A is a simplified view of the prosthetic heart valve 100 initially loaded to the delivery device 350. The cords 132a-132c are each routed from the spindle 354, wound or wrapped about a circumference of the prosthesis 100, and then connected to the release pin 136 commensurate with the descriptions above. FIG. 21A reflects the free end 150 of each of the cords 132a-132c connected to the release pin 136, for example by forming a loop within which the release pin 136 is slidably received. The connectors 356 are attached to a frame of the stented prosthetic heart valve 100 and interface with the release pin 136. In this regard, the connectors 356 are sized such that when engaged with the release pin 136, the release pin 136 is drawn against the spindle 354, and the spindle 354 in turn is drawn against the prosthesis 100. In the tethered and expanded state of FIG. 21A, then, the spindle 354 is effectively locked to selected location of the prosthetic valve 100. The cords 132a-132c are tensioned to collapse or crimp the stented prosthetic heart valve 100 for delivery to a target site; tension in the cords 132a-132c is released to effectuate deployment.

Figure 21B:
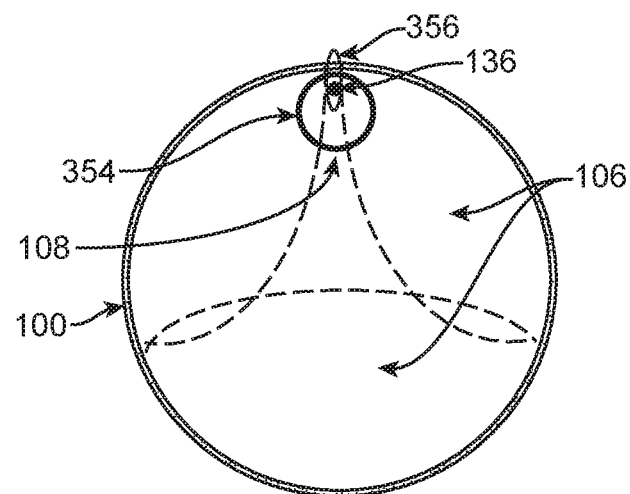
FIG. 21B is a simplified lateral cross-sectional view of the arrangement of FIG. 21A.

A rotational arrangement of the stented prosthetic heart valve 100 relative to the release pin 136 as established by the connectors 356 can be selected to align the spindle 354 with structural features of the prosthesis 100. For example, FIG. 21B illustrates the leaflets 106 of the prosthesis 100 with phantom lines; one of the commissures 108 defined at two of the leaflets 106 is also generally identified. The prosthesis 100 has been rotationally arranged and secured to the release pin 136 by the connector 356 such that the spindle 354 is located, and effectively locked, at the commissure 108. In the tethered and expanded state of FIG. 21B, the spindle 354 will not overtly interfere with functioning of the prosthesis, permitting meaningful evaluation by a clinician prior to full release of the stented prosthetic heart valve 100 from the delivery device 350. The release pin 136 can subsequently be removed from engagement with the connectors 356 and the cords 132a-132c (FIG. 21A), thereby fully releasing the prosthesis 100 from the delivery device 350.

Figure 22A:
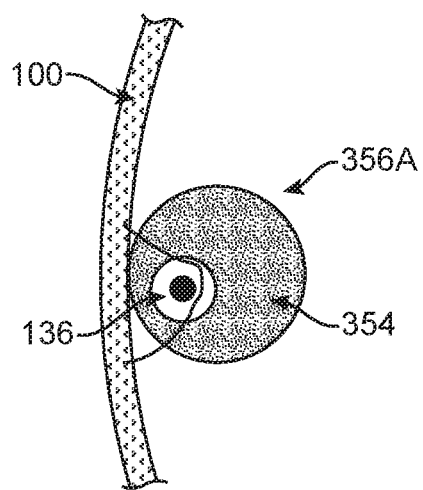
FIG. 22A is a simplified lateral cross-sectional view of a portion of another delivery device in accordance with principles of the present disclosure connected to a stented prosthetic heart valve in a tethered and expanded state.
Figure 22B:
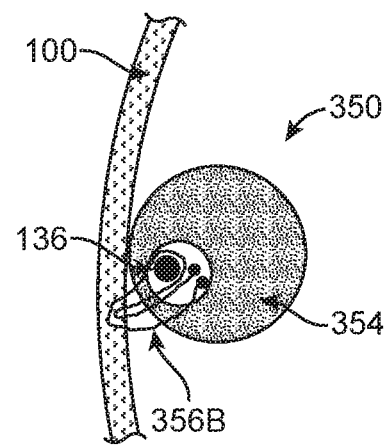
FIG. 22B is a simplified lateral cross-sectional view of a portion of another delivery device in accordance with principles of the present disclosure connected to a stented prosthetic heart valve in a tethered and expanded state.

In some embodiments, the connectors 356 remain with the implanted stented prosthetic heart valve 100, and can be routed or otherwise coupled with a frame of the prosthesis 100 in various manners. For example, FIG. 22A provides a simplified illustration of another embodiment connector 356A coupled to the stented prosthetic heart valve 100 and threaded about the release pin 136. As with the embodiment and arrangement of FIG. 21B, in the tethered and expanded state of FIG. 22A, connection between the connector 356A and the release pin 136 holds or locks the spindle 354 against the prosthesis 100 at a selected location (e.g., a commissure). When the release pin 136 is subsequently manipulated to release the cords (not shown), the connector 356A is also disengaged from the release pin 136. In other embodiments, the connector(s) 356A-356B can be configured to be permanently connected with the spindle 354 (and thus do not remain with the prosthesis 100 upon final implantation). For example, FIG. 22B illustrates another connector 356B format in accordance with the present disclosure. The connector 356B is permanently attached to the spindle 354 and is routed about the release pin 136 and the prosthesis 100 in the tethered and expanded state shown. When the release pin 136 is subsequently manipulated to release the cords (not shown), the connector 356B is also disengaged from the release pin 136. The connector 356B can then be removed from the deployed prosthesis 100 along with the delivery device 350.

Figure 23:
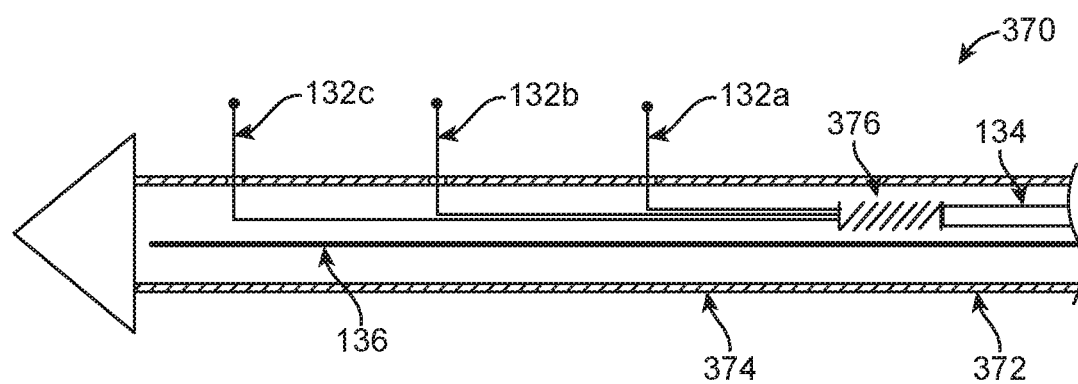
FIG. 23 is a simplified cross-sectional view of a portion of another delivery device in accordance with principles of the present disclosure.

Portions of another embodiment delivery device 370 in accordance with principles of the present disclosure are shown in simplified form in FIG. 23. The delivery device 370 is akin to previous embodiments and includes an inner shaft 372 forming or carrying a spindle 374, the plurality of cords 132a-132c, the optional tension control rod 134, the release pin 136, and a handle assembly (not shown, but akin to the handle assembly 138 (FIG. 2) described above). In addition, the delivery device 370 includes one or more springs 376 for maintaining tension in one or more of the cords 132a-132c as described below.

With the non-limiting embodiment of FIG. 23, the spring 376 is commonly connected to, and thus acts upon, all of the cords 132a-132c. In other embodiments, the spring 376 can act upon less than all, optionally one, of the cords 132a-132c. In related embodiments, one or more additional springs can be included, with each spring being connected to a respective one of the cords 132a-132c. Further, while the spring 376 is generally shown as located within or adjacent the spindle 374, between the cords 132a-132c and the tension control rod 134, other locations are equally acceptable. For example, the spring(s) 376 can be located within the inner shaft 372 (proximal the spindle 374), within the handle assembly 138 (FIG. 2), etc. In yet other embodiments, the tension control rod 134 is omitted and the spring(s) 376 is interposed along a length of one or more of the cords 132a-132c.

Figure 24A:
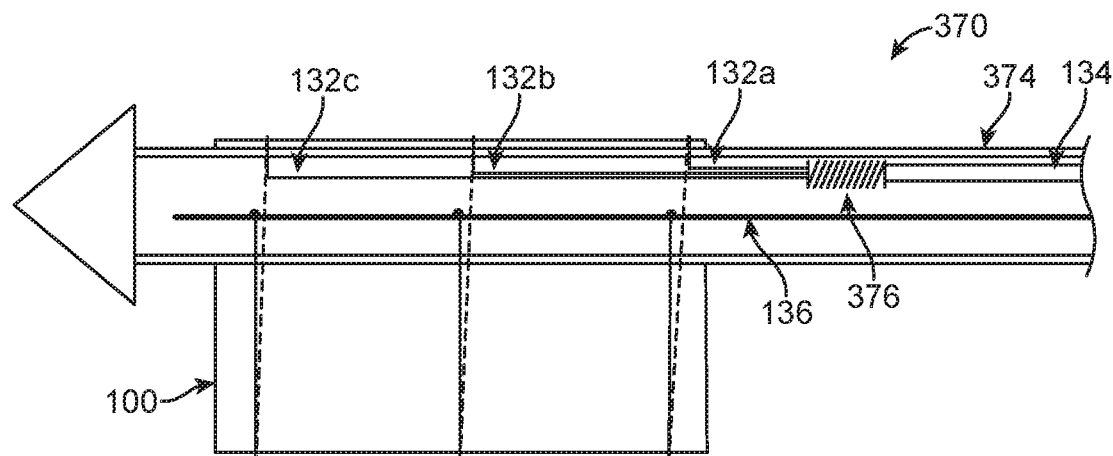
FIG. 24A is a simplified cross-sectional view of a stented prosthetic heart valve and the delivery device of FIG. 23 in a tethered and expanded state.

A stented prosthetic heart valve can be coupled or loaded to, and subsequently deployed from, the delivery device 370 in manners akin to the descriptions above. For example, FIG. 24A is a simplified view of the prosthetic heart valve 100, in the normal, expanded condition, loaded to the delivery device 370. The cords 132a-132c are each extended from the spindle 374, wound or wrapped about a circumference of the prosthesis 100, and then connected to the release pin 136 commensurate with the descriptions above. Regardless of the number provided and location, the spring(s) 376 is configured (e.g., spring force, length, etc.) to maintain a slight tension in one or more of the cords 132a-132c. That is to say, in the tethered and expanded state of FIG. 24A, the spring(s) 376 take up slack in one or more of the cords 132a-132c, thus holding the spindle 374 against the stented prosthetic heart valve 100. In this regard, the prosthesis 100 can be rotationally arranged relative to the spindle 374 such that the spindle 374 is held in a commissure of the stented prosthetic heart valve 100 (not shown, but akin to the relationship described above with respect to FIG. 21B). Only a slight amount of tension is created by the spring(s) 376 (in the tethered and expanded state). In some embodiments, the spring(s) 376 allow or provide enough tension in the cords 132a-132c such that the cords 132a-132c are never over-loosened or exhibit slack in wrapping about the prosthetic heart valve 100 (in the tethered and expanded state). As a point of reference, any slackness in the cords 132a-132c might undesirably allow the cords 132a-132c to become entangled with the patient's anatomy (e.g., a calcium chunk) or with a portion of the valve 100, especially under the pulsatile pressures of the cardiac cycle. However, presence of the spring(s) 376 does not cause the cords 132a-132c to overtly impede or prevent the prosthesis 100 from attaining the normal, expanded condition.

Figure 24B:
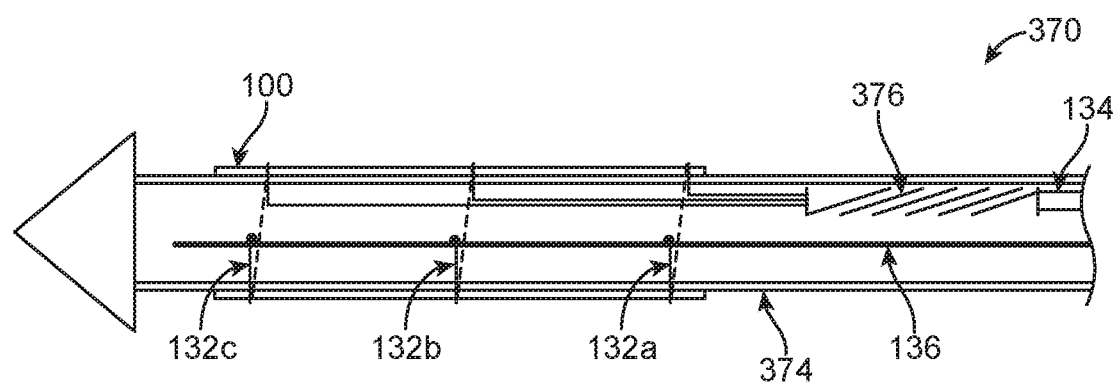
FIG. 24B is a simplified side view of the components of FIG. 24A in a delivery state, including the stented prosthetic heart valve cinched to a compressed condition.

The delivery device 370 can further be operated to compress or cinch the prosthesis 100 onto the spindle 374 in accordance with the descriptions above. For example, and as shown in FIG. 24B, the tension control rod 134 is proximally retracted, tensioning the cords 132a-132c to compress the stented prosthetic heart valve 100. In this regard, the spring(s) 376 is configured (e.g., spring force constant, length, etc.) to transfer forces from the tension control rod 134 onto the cords 132a-132c sufficient for compressing the prosthesis 100.

Figure 25:
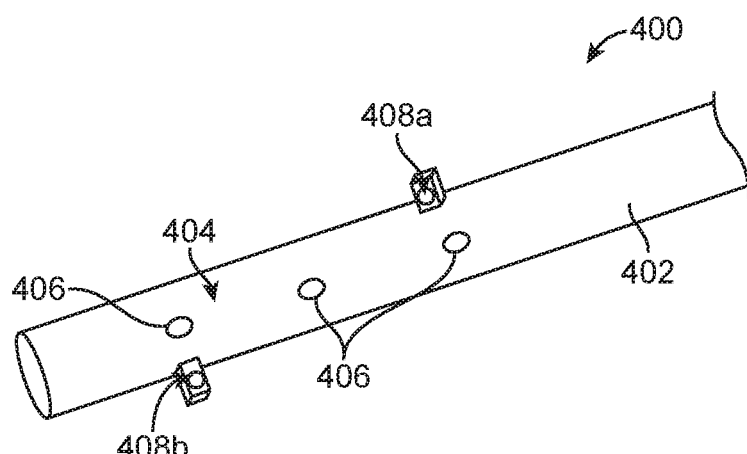
FIG. 25 is a simplified perspective view of a portion of another delivery device in accordance with principles of the present disclosure.

Portions of another embodiment delivery device 400 in accordance with principles of the present disclosure are shown in simplified form in FIG. 25. The delivery device 400 is akin to other embodiments and includes an inner shaft 402 forming or carrying a spindle 404, along with cords (not shown), an optional tension control rod (not shown), an optional release pin (not shown), and a handle assembly (not shown). As with previous embodiments, the spindle 404 forms openings 406 through which respective ones of the cords can be threaded to and from an exterior of the spindle 404 commensurate with the descriptions above. In addition, the delivery device 400 includes one or more anchors, such as anchors 408a, 408b (shown schematically in FIG. 25). The anchors 408a, 408b are placed on and extend from an exterior of the spindle 404, and are configured to selectively lock the spindle 404 to a frame of a stented prosthetic heart valve. In some embodiments, the anchors 408a, 408b can include apertures through which a retention suture or the like (not shown) would pass to secure the spindle 404 to the stent frame.

Figure 26A:
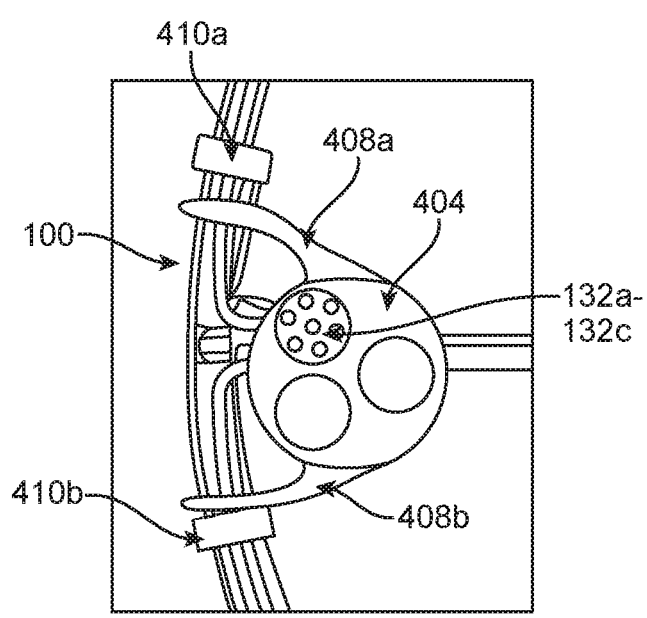
FIG. 26A is a simplified lateral cross-sectional view of a stented prosthetic heart valve and the delivery device of FIG. 25 in a tethered and expanded state.
Figure 26B:
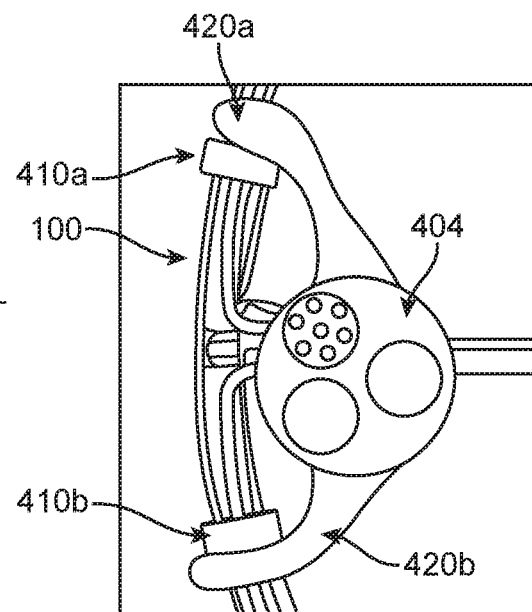
FIG. 26B is a simplified lateral cross-sectional view of a portion of another delivery device in accordance with principles of the present disclosure in a tethered and expanded state, including a stented prosthetic heart valve in a normal, expanded condition loaded to the delivery device.

In one example, FIG. 26A illustrates the prosthesis 100 in a tethered and expanded state relative to the delivery system 400. The anchors 408a, 408b are configured and arranged to bear against protrusions 410a, 410b of the stent frame of the stented prosthetic heart valve 100 (e.g., the anchors 408a, 408b exhibit an outward bias, thereby frictionally securing the anchors 408a, 408b against the protrusions 410a, 410b). The anchors 408a, 408b can be further secured or tethered to the frame by one or more of the cords 132a-132c (referenced generally in FIG. 26A). Regardless, in the tethered and expanded state, connection between the anchors 408a, 408b and the prosthesis 100 holds or locks the spindle 404 against the stented prosthetic heart valve 100 at a selected location (e.g., a commissure). The anchors 408a, 408b (and thus the spindle 404) are released from the prosthesis 100 with removal of the cords 132a-132c. FIG. 26B illustrates a related embodiment in which anchors 420a, 420b are again carried by the spindle 404 and are configured to interface with the protrusions 410a, 410b. With this alternative embodiment, the anchors 420a, 420b are configured to exhibit an inward bias to robustly engage the protrusions 410a, 410b.

Figure 27:
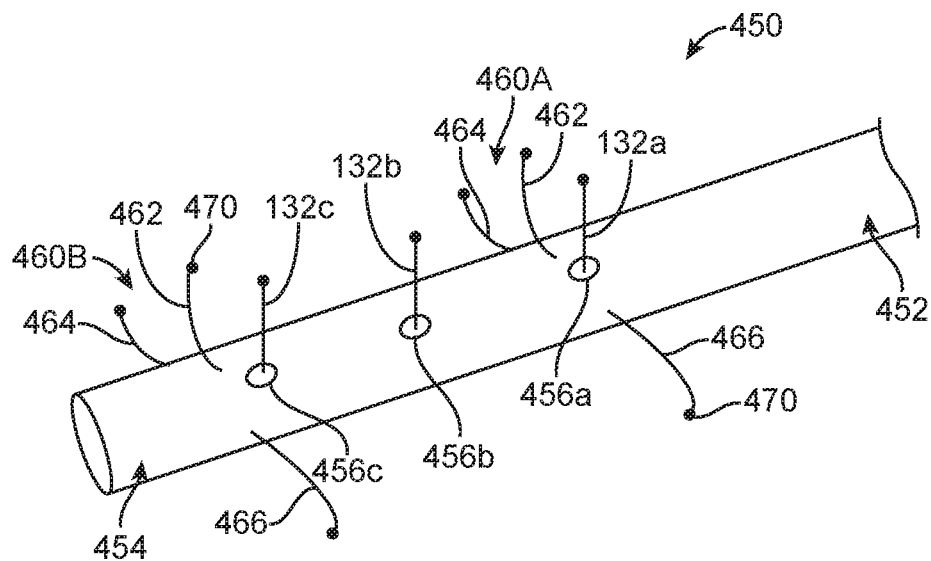
FIG. 27 is a simplified perspective view of a portion of another delivery device in accordance with principles of the present disclosure.

Portions of another embodiment delivery device 450 in accordance with principles of the present disclosure are shown in simplified form in FIG. 27. The delivery device 450 is akin to other embodiments and includes an inner shaft 452 forming or carrying a spindle 454, along with the cords 132a-132c, an optional tension control rod (not shown), the optional release pin 136 (hidden in FIG. 26), and a handle assembly (not shown). As with previous embodiments, the spindle 454 forms openings 456a-456c through which respective ones of the cords 132a-132c can be routed to and from an exterior of the spindle 454 commensurate with the descriptions above. In addition, the delivery device 450 includes one or more sets of tethers, such as tether sets 460A, 460B (referenced generally). The first set 460A is located proximate the proximal-most cord opening 456a, and the second set 460B is located proximate the distal-most cord opening 456c. In other embodiments, more or less than two of the tether sets can be provided.

The tether sets 460A, 460B can be identical in some embodiments, and each includes a plurality of tethers, such as tethers 462, 464, 466. Each of the tethers 462-466 is attached or affixed to the spindle 454, and extends from the spindle 454 to a free end 470. The tethers 462-466 are thin, flexible, and substantially inelastic bodies (e.g., sutures, wires, filaments, etc.), and are substantially equidistantly spaced (i.e., within 10 degrees of equidistant spacing) about a circumference of the spindle 454. For example, with some embodiments in which the tether sets 460A, 460B each includes three of the tethers 462-464, arrangement of the tethers 462-466 establishes an approximately 120 degree spacing. While the tethers 462-466 are generally shown as being attached to an exterior of the spindle 454 (e.g., adhesive, weld, etc.), other coupling formats are also acceptable, such as the tethers 462-466 being attached to an interior of the spindle 454.

Figure 28:
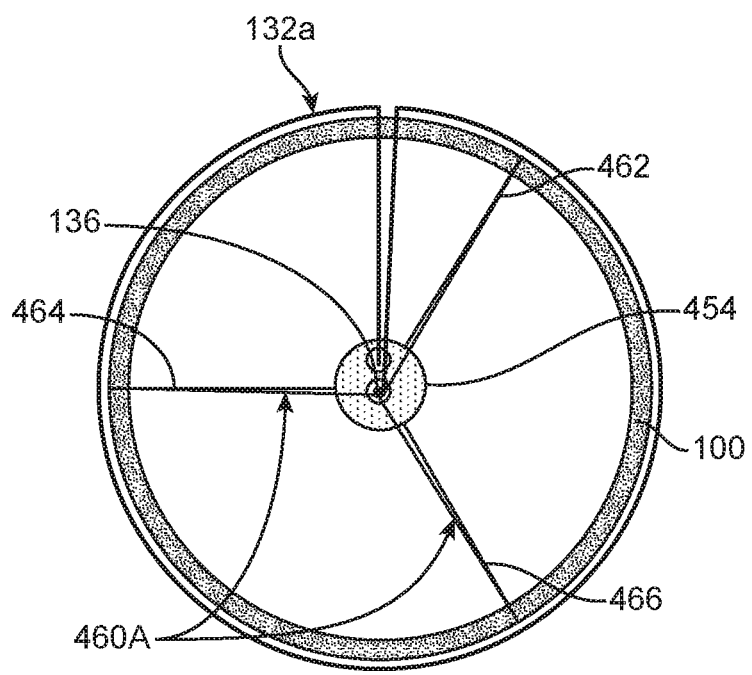
FIG. 28 is a simplified lateral cross-sectional view of a stented prosthetic heart valve and the delivery device of FIG. 27 in a tethered and expanded state.

FIG. 28 is a simplified cross-sectional view of the delivery device 450 coupled to the stented prosthetic heart valve 100, with the prosthesis 100 in the tethered and expanded state. For ease of understanding, FIG. 28 depicts the first tether set 460A and the first cord 132a. Commensurate with previous descriptions, the first cord 132a extends from the spindle 454, wraps around or is otherwise connected to a circumference of the prosthesis 100, and is selectively engaged by the release pin 136. The first-third tethers 462-466 each extend from the spindle 454, are connected to the frame of the stented prosthetic heart valve 100, and are selectively engaged with the release pin 136. For example, and with additional reference to FIG. 27, the free end 470 of each of the tethers 462-466 can form or carry a loop that is slidably received over the release pin 136. The tethers of the second tether set 460B are similarly connected with the prosthesis 100. A length of each of the tethers 462-466 is selected based on an expected radius or geometry of the stented prosthetic heart valve 100 in the expanded condition; more particularly, a length of each of the tethers 462-466 is such that in the tethered and expanded state of FIG. 28, the tethers 462-466 are slightly taut. With this configuration, the tethers 462-466 act in concert to pull the spindle 454 into a center of the prosthetic heart valve 100. A similar relationship is established at a distal side of the prosthesis 100 via the second tether set 460B (FIG. 27). Retraction of the release pin 136 disengages the tethers 462-466 (as well as the cords 132a-132c), allowing the tethers 462-466 to be removed from the deployed stented prosthetic heart valve 100 with retraction of the spindle 454.

Figure 29A:
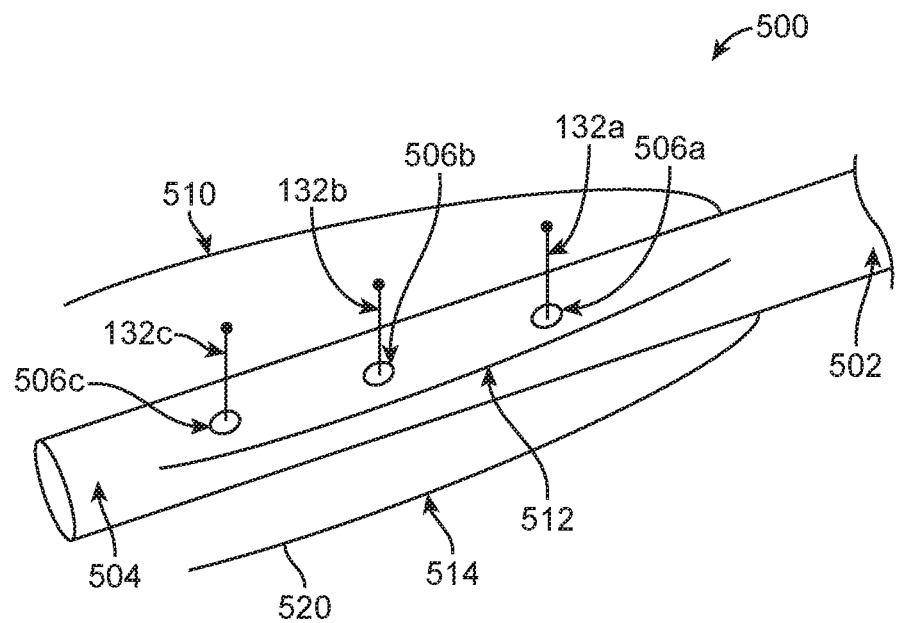
FIG. 29A is a simplified perspective view of a portion of another delivery device in accordance with principles of the present disclosure.

Portions of another embodiment delivery device 500 in accordance with principles of the present disclosure are shown in simplified form in FIG. 29A. The delivery device 500 is akin to embodiments described above and includes an inner shaft 502 forming or carrying a spindle 504, along with the cords 132a-132c, an optional tension control rod (not shown), an optional release pin (not shown), and a handle assembly (not shown). As with previous embodiments, the spindle 504 forms openings 506a-506c through which respective ones of the cords 132a-132c can be threaded to and from an exterior of the spindle 504 commensurate with the previous descriptions. In addition, the delivery device 500 includes a plurality of biasing arms, such as biasing arms 510-514. The biasing arms 510-514 each are attached to and extend from the spindle 504, terminating at a free end 520. The arms 510-514 are thin and flexible bodies with a shape memory configuration that generates a radially outward bias at the corresponding free end 520 (e.g., the arms 510-514 are akin to spring wires). Further, the biasing arms 510-514 are substantially equidistantly spaced (i.e., within 10 degrees of equidistant spacing) about a circumference of the spindle 504. For example, with some embodiments in which three of the biasing arms 510-514 are provided, arrangement of the biasing arms 510-514 establishes an approximately 120 degree spacing. The biasing arms 510-514 can be attached to an exterior of the spindle 404 using conventional techniques (e.g., adhesive, weld, etc.), and are sized and arranged to located the corresponding free end 520 spatially proximate the distal-most cord opening 506c. Other spatial locations between the proximal-most opening 506a and the distal-most opening 506c are also acceptable.

The delivery device 500 is coupled to a stented prosthetic heart valve (not shown) in accordance with previous descriptions, including the cords 132a-132c each wrapped about or connected to a circumference of the prosthesis. The biasing arms 510-514 are located centrally within the so-loaded prosthesis. In the tethered and expanded state (i.e., when the cords 132a-132c remain connected to the prosthesis, and a tension in the cords 132a-132c is sufficiently reduced to allow the prosthesis to self-expand to the normal, expanded condition), the biasing arms 510-514 bear against an interior of the prosthesis, collectively forcing or directing the spindle 504 toward a center of the expanded prosthesis. The delivery device 500 can optionally include an outer sheath (not shown) that is advanced over the biasing arms 510-514 following deployment of the stented prosthetic heart valve, directing the arms 510-514 radially inwardly for removal of the delivery device 500 from the patient.

Figure 29B:
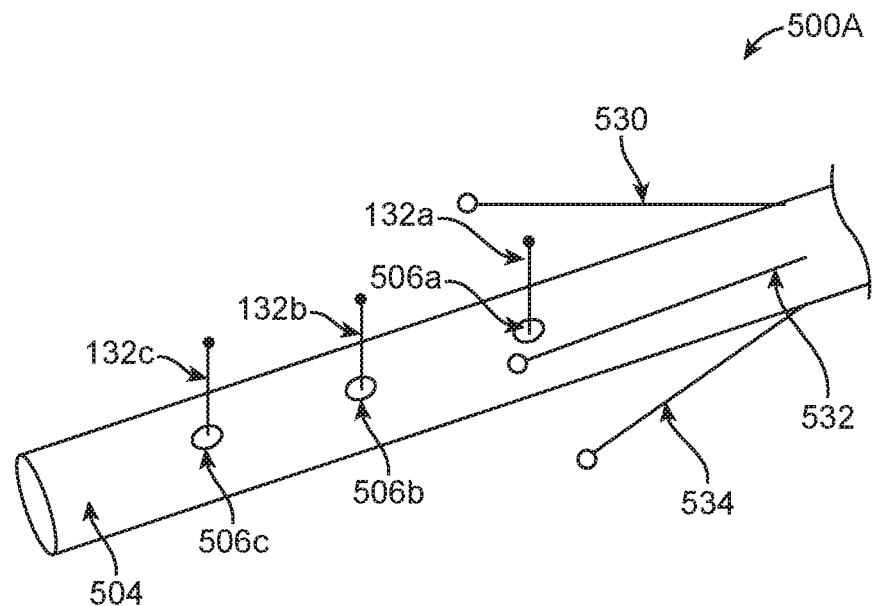
FIG. 29B is a simplified perspective view of a portion of another delivery device in accordance with principles of the present disclosure.

The biasing arms 510-514 can assume other shapes or configurations, and can be fixed to the spindle 504 at other locations. For example, FIG. 29B is a simplified view of an alternative delivery device 500A having biasing arms 530-534 that are highly akin to the biasing arms 510-514 (FIG. 29A) described above but have different shape and are located to extend spatially proximate the proximal-most cord opening 506a.

The delivery device 500A (as well as several other delivery devices of the present disclosure as described above including the delivery device 200 (FIG. 7), the delivery device 300 (FIG. 14A), the delivery device 450 (FIG. 27), and the delivery device 500 (FIG. 29A)) is configured to locate the spindle 504 at an approximate center of the stented prosthetic heart valve in the tethered and expanded state. In other embodiments of the present disclosure, and returning to FIG. 4, the spindle 140 is configured to float or move in response to native blood flow or pressure, thus naturally moving to the center of the expanded prosthesis when in located in a patient's vasculature while retaining the prosthesis in the tethered and expanded state. For example, the spindle 140 can be constructed to have a relatively low mass or weight, and is flexibly connected with a remainder of the inner shaft 130 so as to freely move or float relative to a remainder of the inner shaft 130. By removing inherent rigidity from the spindle 140, the spindle 140 will naturally move toward the center of the expanded prosthesis in response to native blood flow.

Figure 30C:
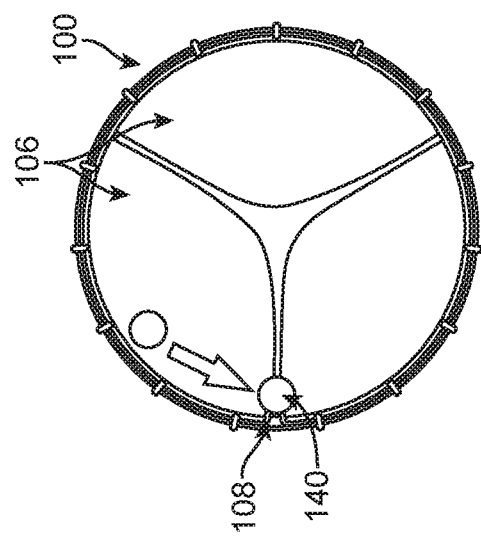
FIGS. 30A-30C illustrate operation of another delivery device in accordance with principles of the present disclosure in a tethered and expanded state relative to a stented prosthetic heart valve in a normal, expanded condition loaded to the delivery device.
Figure 30B:
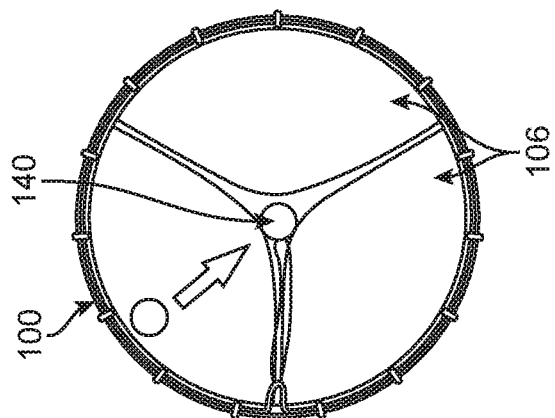
Figure 30A:
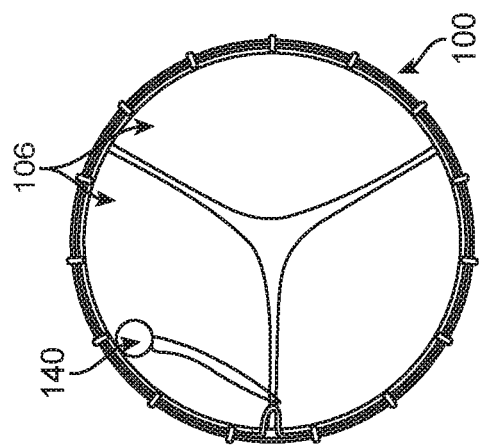

In yet other embodiments, the delivery device 120 includes or incorporates a steering mechanism configured to facilitate user-actuated movement of the spindle 140 to a desired spatial location. For example, pull wires, a steering sheath, etc. can be included. FIG. 30A illustrates the spindle 140 and the prosthesis 100 in the tethered and expanded state; a location of the spindle 140 may interfere with coapting or functioning of the leaflets 106. With embodiments in which the delivery device includes a spindle steering feature, the spindle 140 can be directed or steered to a center of the prosthesis 100 as in FIG. 30B. Alternatively, the spindle 140 can be directed or steered to one of the commissures 108 of the prosthesis 100 as in FIG. 30C. With the spindle 140 desirably located relative to the leaflets 106, hemodynamics of the prosthetic valve 100 can be accurately assessed.

Figure 31:
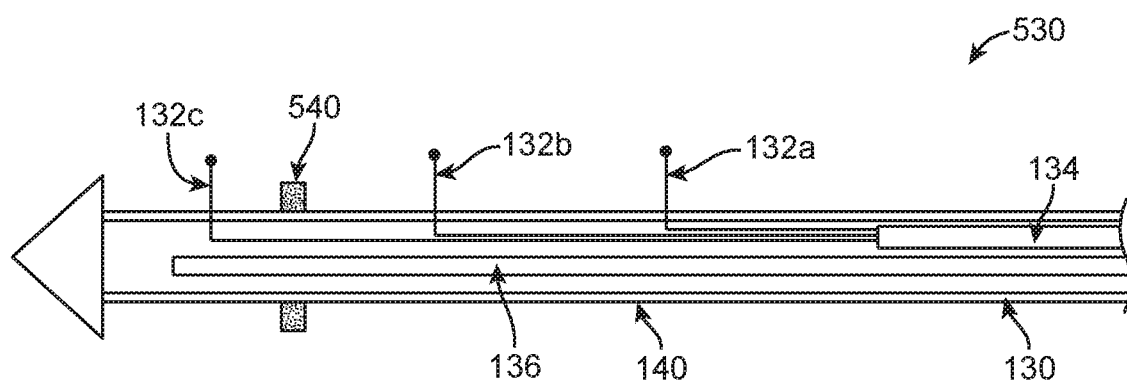
FIG. 31 is a simplified cross-sectional view of a portion of another delivery device in accordance with principles of the present disclosure.

Portions of another embodiment delivery device 530 in accordance with principles of the present disclosure are shown in simplified form in FIG. 31. The delivery device 530 is akin to other embodiments, and includes the inner shaft 130 forming or carrying the spindle 140, the cords 132a-132c, the optional tension control rod 134, the optional release pin 136, and the handle assembly 138 (FIG. 2). In addition, the delivery device 530 includes a valve 540 assembled to and projecting from the spindle 140. The valve 540 can assume a variety of forms conducive to forming a seal with prosthetic leaflets, and may or may not include a valve-type mechanism. In some embodiments, the valve 540 is entirely exterior the spindle 140 (e.g., akin to an O-ring or gasket); in other embodiments, one or more components or bodies of the valve 540 are located within the spindle 140 for selectively closing or sealing lumen(s) of the spindle 140. In yet other embodiments, the valve 540 can include or be acted upon by an actuator that operates to radially expand and contract the valve 540 relative to an exterior of the spindle 140. A location of the valve 540 along a length of the spindle 140 corresponds with an expected location of certain features of a prosthesis (not shown) retained by the delivery device 530 as described in greater detail below. In more general terms, while the valve 540 is illustrated in FIG. 31 as being located adjacent the distal-most cord 132c, other longitudinal locations along the spindle 140 are equally acceptable.

Figure 32:
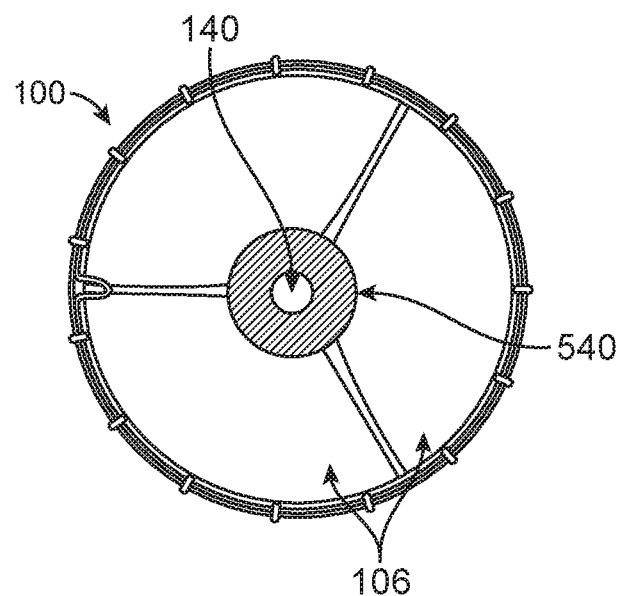
FIG. 32 is a simplified end view of a stented prosthetic heart valve and the delivery device of FIG. 31 in a tethered and expanded state.

FIG. 32 illustrates the stented prosthetic heart valve 100 retained to the spindle 140 in the tethered and expanded state. The valve 540 creates a seal with the leaflets 106 of the prosthesis 100. In other words, when deployed at a vascular target site, the leaflets 106 close on to the valve 540 in response to native blood flow, facilitating hemodynamic evaluation. The valve 540 can be incorporated into any of the delivery device embodiments of the present disclosure, including those configured to center the corresponding spindle relative to the prosthesis in the tethered and expanded state.

Figure 33:
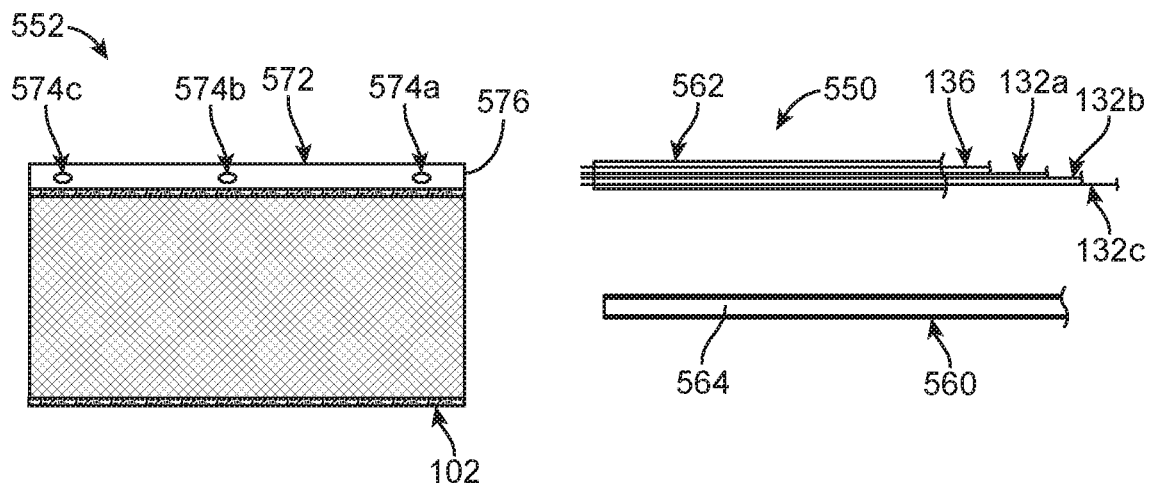
FIG. 33 is a simplified side view of portions of another delivery device in accordance with principles of the present disclosure along with a stented prosthetic heart valve.

Portions of another embodiment delivery device 550 in accordance with principles of the present disclosure are shown in simplified form in FIG. 33, along with a stented prosthetic heart valve 552. The delivery device 550 includes a center shaft 560, a coupling tube 562, the cords 132a-132c, the optional tension control rod (not shown), the release pin 136, and the handle assembly 138 (FIG. 2). The center shaft 560 forms a lumen 564, for example for receiving a guide wire (not shown). The coupling tube 562 is slidably associated with the center shaft 560. For example, the center shaft 560 and the coupling tube 562 can be slidably disposed within an outer sheath (not shown), can be slidably connected to one another at proximal portions thereof, etc. Regardless, the coupling tube 562 forms one or more lumens within which the cords 132a-132c and the release pin 136 are slidably disposed. Further, the coupling tube 562 is configured for releasable connection with a corresponding component carried by the stented prosthetic heart valve 552 as described below.

The stented prosthetic heart valve 552 is generally of a conventional design (i.e., akin to the stented prosthetic heart valve 100 (FIG. 1A)), including the stent frame 102 carrying one or more leaflets (not shown) as described above. Further, a spindle 572 is attached to an exterior or exterior surface of the stent frame 102. The spindle 572 is akin to the spindles described elsewhere in the present disclosure, except that with the embodiment of FIG. 33, the spindle 572 is permanent component of the stented prosthetic heart valve 552. The spindle 572 forms a plurality of cord openings 574a-574c through which respective ones of the cords 132a-132c can be routed to and from an exterior of the spindle 572 commensurate with the previous descriptions.

The spindle 572 includes or forms a coupling structure (not shown) at a proximal end 576, configured for complimentary connection with a coupling structure (not shown) formed or carried by the coupling tube 562. For example, the coupling tube 562 and the spindle 572 can be releasably coupled by a mechanism or structure establishing a friction fit, a twist-type connection, etc.

The prosthesis 552 is mounted to the delivery device 550 by routing the cords 132a-132c from the coupling tube 562 into the spindle 572, through a corresponding one of the cord openings 574a-574c and then wrapped around or connected to a circumference of the stent frame 102 akin to the descriptions above. The so-arranged cords 132a-132c are threaded back into the spindle 572 and into selective engagement with the release pin 136. In this regard, the release pin 136 can be advanced into the spindle 572 for engaging the cords 132a-132c, or the cords 132a-132c can be fed back into the coupling tube 562 and engaged with the release pin 136. The coupling tube 562 and the spindle 572 are then attached to one another as described above. Finally, the center shaft 560 is centrally disposed within the prosthesis 552.

Figure 34A:
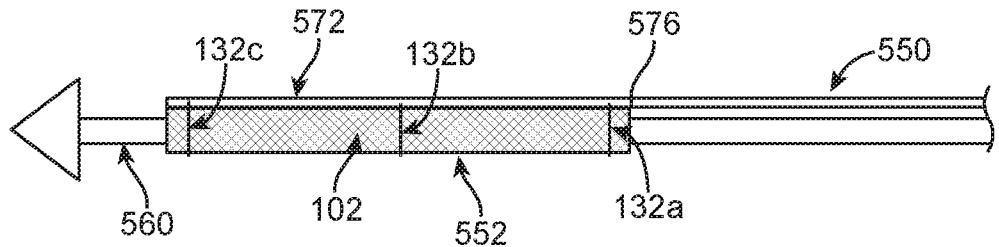
FIG. 34A is a simplified side view of the delivery device and stented prosthetic heart prosthetic heart valve of FIG. 33 in a loaded, delivery state.
Figure 34B:
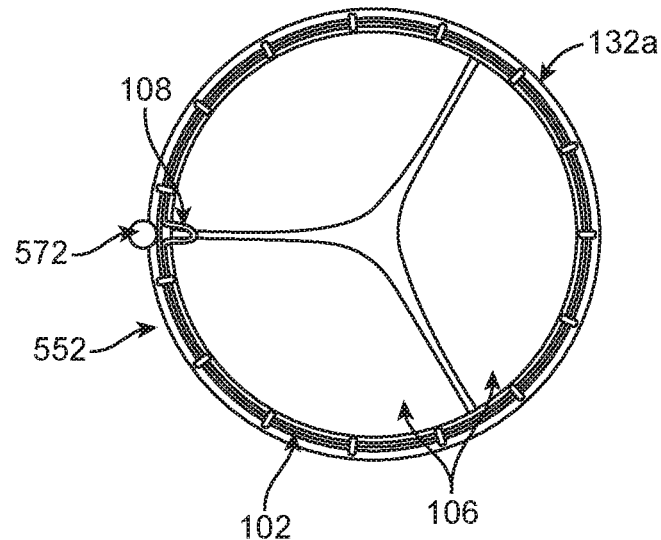
FIG. 34B is a simplified end view of the delivery device and stented prosthetic heart valve of FIG. 33 in a tethered and expanded state.

As shown in FIG. 34A, tension applied to the cords 132a-132c causes the stented prosthetic heart valve 552 to compress or crimp onto the center shaft 560. The spindle 572 remains at an exterior of the stent frame 102. In an initial stage of deployment, tension in the cords 132a-132c is lessened or reduced, allowing the stent frame 102 to self-expand toward the normal, expanded condition. The center shaft 560 can then be withdrawn from within the prosthesis 552. In the tethered and expanded state of FIG. 34B, the prosthesis 552 remains connected or tethered to the delivery device (primary hidden in the view) via the cords (the first cord 132a is visible in FIG. 34B, and is shown as being slightly spaced from the stent frame 102 for ease of understanding) extending from the spindle 572. Because the spindle 572 is located outside of the stent frame 102, a meaningful evaluation of the prosthetic valve 552 can be obtained as the spindle 572 does not interfere with functioning or coapting of the leaflets 106. With additional reference to FIG. 33, the delivery device 550 can be completely released from the stented prosthetic heart valve 552 by retracting the release pin 136, in turn allowing the cords 132a-132c to be withdrawn from the spindle 572. The coupling tube 562 is disconnected from the spindle 572, and the delivery device 550 removed from the patient. The spindle 572 remains with the prosthetic heart valve 552 upon final implantation, and can be located at one of the commissures 108 in some embodiments.

Figure 35:
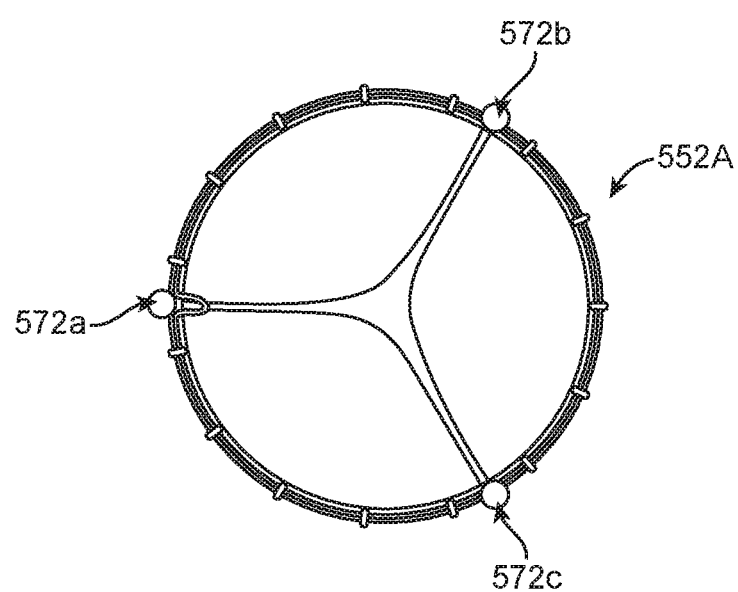
FIG. 35 is a simplified end view of another delivery device and stented prosthetic heart valve in accordance with principles of the present disclosure and in a tethered and expanded state.

While the delivery device 550 has been described as including a single coupling tube 562 interfacing with a single spindle 572 provided with the stented prosthetic heart valve 552, in other embodiments, two or more of coupling tubes (and a corresponding number of spindles) can be provided, for example, one coupling tube/spindle for each of the cords 132a-132c. For example, FIG. 35 is a simplified representation of a stented prosthetic heart valve 552A akin to the prosthesis 552 of FIG. 34B, but including three spindles 572a-572c. The corresponding delivery device (not shown) includes three coupling tubes (each akin to the coupling tube 562 (FIG. 33), each carrying a respective one of the cords 132a-132c (FIG. 33). Upon final deployment and implant, the spindles 572a-572c remain with the prosthesis 552A.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthetic heart valve including a valve structure carried by a stent frame configured to self-expand from a collapsed condition to a normal, expanded condition, the delivery device comprising:
    an inner shaft forming a lumen;
    a spindle extending from the inner shaft along a spindle axis, wherein the spindle defines a first hole open to the lumen and an exterior of the spindle, and a second hole open to the lumen and the exterior of the spindle, and the second hole is distally spaced from the first hole in an axial direction of the spindle axis;
    a first cord slidably disposed within the lumen and extending through the first hole for selectively cinching the stented prosthetic heart valve at a first axial location of the stented prosthetic heart valve;
    a second cord slidably disposed within the lumen and extending through the second hole for selectively cinching the stented prosthetic heart valve at a second axial location of the stented prosthetic heart valve, wherein the second axial location is distally spaced from the first axial location in the axial direction of the spindle axis; and
    a lateral control feature configured to bias the spindle to a selected lateral location relative to the stented prosthetic heart valve tethered to the spindle in a tethered and expanded state, wherein the lateral control feature includes a first spring configured to apply a tension to the first cord and a tension to the second cord.

2. The delivery device of claim 1, further comprising a third cord and the spindle defines a third hole open to the lumen and the exterior of the spindle, wherein the third cord is slidably disposed within the lumen and extends through the third hole for selectively cinching the stented prosthetic heart valve at a third axial location of the stented prosthetic heart valve, wherein the third axial location is distally spaced from the second axial location in the axial direction of the spindle axis.

3. The delivery device of claim 2, wherein the first spring is further configured to apply a tension to the third cord.

4. The delivery device of claim 1, further comprising a handle assembly, wherein the lateral control feature is located within the handle assembly.

5. The delivery device of claim 1, wherein the lateral control feature comprises a tension control rod.

6. The delivery device of claim 5, wherein the first spring interconnects the tension control rod to the first cord and the second cord.

7. The delivery device of claim 1, further comprising a release pin, wherein the first cord is releasably connected to the release pin.

8. The delivery device of claim 7, wherein the second cord is releasably connected to the release pin.

9. A delivery device for delivering a stented prosthetic heart valve including a valve structure carried by a stent frame configured to self-expand from a collapsed condition to a normal, expanded condition, the delivery device comprising:
  an inner shaft forming a lumen;
  a spindle extending from the inner shaft along a spindle axis, wherein the spindle defines a first hole open to the lumen and an exterior of the spindle, and a second hole open to the lumen and the exterior of the spindle, and the second hole is distally spaced from the first hole in an axial direction of the spindle axis;
  a first cord slidably disposed within the lumen and extending through the first hole for selectively cinching the stented prosthetic heart valve at a first axial location of the stented prosthetic heart valve;
  a second cord slidably disposed within the lumen and extending through the second hole for selectively cinching the stented prosthetic heart valve at a second axial location of the stented prosthetic heart valve, wherein the second axial location is distally spaced from the first axial location in the axial direction of the spindle axis; and
  a lateral control feature configured to bias the spindle to a selected lateral location relative to the stented prosthetic heart valve tethered to the spindle in a tethered and expanded state, wherein the lateral control feature includes a first spring configured to apply a tension to the first cord, and the first spring is located within the spindle and interconnects the first cord to a tension control rod.

10. A delivery device comprising:
  a stented prosthetic heart valve including a valve structure carried by a stent frame configured to self-expand from a collapsed condition to a normal, expanded condition;
  an inner shaft forming a lumen;
  a spindle extending from the inner shaft along a spindle axis, wherein the spindle defines a first hole open to the lumen and an exterior of the spindle, and a second hole open to the lumen and the exterior of the spindle, and the second hole is distally spaced from the first hole in an axial direction of the spindle axis;
  a first cord slidably disposed within the lumen;
  a second cord slidably disposed within the lumen;
  a lateral control feature biasing the spindle to a selected lateral location relative to the stented prosthetic heart valve tethered to the spindle in a tethered and expanded state; wherein the lateral control feature includes a first spring applying tension to the first cord and the second cord; and
  wherein the first cord extends through the first hole and is wrapped around a circumference of the stented prosthetic heart valve while cinching the stented prosthetic heart valve at a first axial location of the stented prosthetic heart valve, and the second cord extends through the second hole and is wrapped around the circumference of the stented prosthetic heart valve while cinching the stented prosthetic heart valve at a second axial location of the stented prosthetic heart valve, wherein the second axial location is distally spaced from the first axial location in the axial direction of the spindle axis.

11. The delivery device of claim 10, further comprising a tension control rod; wherein the first spring interconnects the tension control rod to the first cord and the second cord.

12. The delivery device of claim 10, further comprising a release pin, wherein the first cord is releasably connected to the release pin.

13. The delivery device of claim 12, wherein the second cord is releasably connected to the release pin.

\* \* \* \* \*